US011045542B2

(12) United States Patent
Didierlaurent et al.

(10) Patent No.: US 11,045,542 B2
(45) Date of Patent: Jun. 29, 2021

(54) METHOD OF REDUCING REACTOGENICITY INDUCED BY ADMINISTRATION OF VACCINE OR IMMUNOGENIC COMPOSITION

(71) Applicant: GLAXOSMITHKLINE BIOLOGICALS, SA, Rixensart (BE)

(72) Inventors: Arnauld Michel Didierlaurent, Rixensart (BE); Caroline Christiane Herve, Rixensart (BE)

(73) Assignee: GLAXOSMITHKLINE BIOLOGICALS SA, Rixensart (BE)

( * ) Notice: Subject to any disclaimer, the term of this patent is extended or adjusted under 35 U.S.C. 154(b) by 0 days.

(21) Appl. No.: 16/060,659

(22) PCT Filed: Dec. 13, 2016

(86) PCT No.: PCT/EP2016/080754
§ 371 (c)(1),
(2) Date: Jun. 8, 2018

(87) PCT Pub. No.: WO2017/102703
PCT Pub. Date: Jun. 22, 2017

(65) Prior Publication Data
US 2018/0360956 A1    Dec. 20, 2018

(30) Foreign Application Priority Data

Dec. 15, 2015  (GB) ..................... 1522132

(51) Int. Cl.
*A61K 39/39*    (2006.01)
*A61P 31/00*    (2006.01)
*A61K 39/00*    (2006.01)
*A61K 39/002*    (2006.01)
*A61K 39/02*    (2006.01)
(Continued)

(52) U.S. Cl.
CPC ............ *A61K 39/39* (2013.01); *A61K 39/002* (2013.01); *A61K 39/0005* (2013.01); *A61K 39/02* (2013.01); *A61K 39/12* (2013.01); *A61P 31/00* (2018.01); *A61K 45/06* (2013.01); *A61K 2039/555* (2013.01); *A61K 2039/55555* (2013.01); *A61K 2039/55572* (2013.01); *A61K 2300/00* (2013.01); *Y02A 50/30* (2018.01)

(58) Field of Classification Search
CPC ........ A61K 39/39; A61K 39/02; A61K 39/12; A61K 2039/55555; A61P 31/00
See application file for complete search history.

(56) References Cited

FOREIGN PATENT DOCUMENTS

WO    WO 96/33739    * 10/1996

OTHER PUBLICATIONS

Ramon et al. Vaccination with DHA-derived specialized proresolving mediators increases the antibody-mediated immune response against influenza virus. J. Immunol., May 1, 2014, 192, 1 Supplement, 72.3.*

(Continued)

*Primary Examiner* — Anna Pagonakis
(74) *Attorney, Agent, or Firm* — Birch, Stewart, Kolasch & Birch, LLP

(57) ABSTRACT

The invention provides a pro-resolving mediator for use in the reduction of reactogenicity induced by administration of a vaccine or immunogenic composition comprising at least an antigen, and vaccines or immunogenic compositions comprising such a pro-resolving mediator.

21 Claims, 6 Drawing Sheets

(51) Int. Cl.
*A61K 39/12* (2006.01)
*A61K 45/06* (2006.01)

(56) References Cited

OTHER PUBLICATIONS

Isobe et al. Identification and structure determination of novel inflammatory mediator resolvin E3, 17,18-dihydroxyeicosapentaenoic acid. The Journal of Biological Chemistry, vol. 287, No. 13, pp. 10525-10534, Mar. 23, 2012.*
Buckley et al., "Proresolving Lipid Mediators and Mechanisms in the Resolution of Acute Inflammation," Immunity, vol. 40, Mar. 20, 2014, pp. 315-327.
Buckley et al., "The resolution of inflammation," Nature Reviews Immunology, vol. 13, Jan. 2013 (published online Nov. 30, 2012), pp. 59-66.
Herold et al., "Acute lung injury: how macrophages orchestrate resolution of inflammation and tissue repair," Frontiers in Immunology, vol. 2, Article 65, Nov. 2011, pp. 1-13.
Lima-Garcia et al., "The precursor of resolvin D series and aspirin-triggered resolvin D1 display anti-hyperalgesic properties in adjuvant-induced arthritis in rats," British Journal of Pharmacology, vol. 164, 2011, pp. 278-293.
Newson et al., "Resolution of acute inflammation bridges the gap between innate and adaptive immunity," Blood, vol. 124, No. 11, Sep. 11, 2014, pp. 1748-1764 (18 pages total).
Ramon et al., "The Specialized Proresolving Mediator 17-HDHA Enhances the Anitbody-Mediated Immune Response against Influenza Virus: A New Class of Adjuvant," The Journal of Immunology, vol. 193, 2014 (published online Nov. 2014), pp. 6031-6040.
Ramon, "The Effects of Specialized Proresolving Lipid Mediators on B Lymphocyte Function: Implications for B Cell Differentiation and Antibody Production," Thesis Submitted to University of Rochester, 2013, pp. 1-160 (174 pages total).
Serhan et al., "Protectins and maresins: New pro-resolving families of mediators in acute inflammation and resolution bioactive metabolome," Biochimica et Biophysica Acta, vol. 1851, 2015 (published online Aug. 17, 2014), pp. 397-413.
Serhan, "Pro-resolving lipid mediators are leads for resolution physiology," Nature, vol. 510, Jun. 5, 2014, pp. 92-101.
Sugimoto et al., "Resolution of Inflammation: What Controls Its Onset," Frontiers in Immunology, vol. 7, Article 160, Apr. 2016, pp. 1-18.
Yan et al., "Omega-3 Fatty Acids Prevent Inflammation and Metabolic Disorder through Inhibition of NLRP3 Inflammasome Activation," Immunity, vol. 38, No. 6, Jun. 27, 2013, pp. 1154-1163.
Yoo et al., "Resolvins: Endogenously-Generated Potent Painkilling Subtances and their Therapeutic Perspectives," Current Neuropharmacology, vol. 11, No. 6, 2013, pp. 664-676.

* cited by examiner

A

B

A

B

METHOD OF REDUCING REACTOGENICITY INDUCED BY ADMINISTRATION OF VACCINE OR IMMUNOGENIC COMPOSITION

FIELD OF THE INVENTION

The present invention is in the field of vaccines, in particular vaccines with reduced reactogenicity.

BACKGROUND TO THE INVENTION

New compositions or vaccines with an improved immunogenicity are needed to address unmet medical needs. Whilst vaccines beneficially elicit protective immune responses, vaccines can sometimes also result in transient adverse events such as pain at the injection site, swelling and bruising, a phenomenon commonly referred to as reactogenicity. Whilst reactogenicity is transient and not seen as a major safety concern, it may present a barrier to vaccine up-take within a population and thus there is a clear public health benefit to reducing reactogenicity.

Pro-resolving mediators are well known in the art and a number of candidates are in clinical trials for treating, inter alia, ocular and neurodegenerative diseases. Pro-resolving mediators have been reviewed in scientific journals (see Buckley et al. "Proresolving Lipid Mediators and Mechanisms in the Resolution of Acute Inflammation", 2014, *Immunity* 40: 315-327; Serhan "Pro-resolving lipid mediators are leads for resolution physiology", 2014, *Nature* 510: 92-101).

It is an object of the present invention to improve vaccines and immunogenic compositions by reducing their reactogenicity using pro-resolving mediators.

SUMMARY OF THE INVENTION

The present invention provides a pro-resolving mediator defined herein for use in the reduction of reactogenicity induced by administration of a vaccine or an immunogenic composition defined herein.

The invention further provides a method of reducing reactogenicity induced by administration of a vaccine or an immunogenic composition defined herein comprising the step of administering a pro-resolving mediator defined herein.

The invention also provides the use of a pro-resolving mediator defined herein in the manufacture of a medicament to reduce the reactogenicity induced by administration of a vaccine or an immunogenic composition defined herein.

The invention also provides vaccines and immunogenic compositions defined herein comprising at least an antigen defined herein and a pro-resolving mediator defined herein.

The invention further provides kits comprising a pro-resolving mediator defined herein, an antigen defined herein and/or an adjuvant defined herein.

BRIEF DESCRIPTION OF THE DRAWINGS

FIG. 1 shows a graph representing the number of different types of immune cells per muscle collected 24 h after mice received different schemes of injections of an adjuvant and/or RvE1, as indicated on the y axis. Names of the different immune cell types analysed are given next to the graph, with the corresponding colour code. "DCs tot" is for total Dendritic Cells.

FIG. 2 shows a graph representing the number of different types of immune cells per muscle collected 4 h or 24 h after mice received different schemes of injections of an adjuvant and/or MaR1, as indicated on the x axis. Names of the different immune cell types analysed are given next to the graph, with the corresponding colour code. "DCs tot" is for total Dendritic Cells.

FIG. 3 shows a graph representing the concentration of different types of cytokines/chemokines in muscles collected after mice received different schemes of injections of an adjuvant and/or RvE1, as indicated on the y axis. Names of the different cytokine/chemokine types analysed are given next to the graph, with the corresponding colour code. Panel A provides results obtained from muscles collected 4 h after the adjuvant injection. Panel B provides results obtained from muscles collected 24 h after the adjuvant injection.

FIG. 4 shows a graph representing the concentration of different types of cytokines/chemokines in muscle collected 4 h or 24 h after mice received different schemes of injections of an adjuvant and/or MaR1, as indicated on the x axis. Names of the different cytokine/chemokine types analysed are given next to the graph, with the corresponding colour code.

FIG. 5 shows a graph representing the percentage of CD4+ or CD8+ T cells expressing at least two cytokines in mice having received different schemes of vaccination, as indicated on the x axis. Panel A provides results obtained when extracted immune cells were stimulated with the antigen HBS. Panel B provides results obtained when extracted immune cells were stimulated with the antigen OVA.

FIG. 6 shows a graph representing the concentration of IgG antibodies in sera from mice having received different schemes of vaccination, as indicated on the x axis. Panel A provides results obtained using anti-OVA antibodies. Panel B provides results obtained using anti-HBS antibodies.

DETAILED DESCRIPTION

Figure 1:
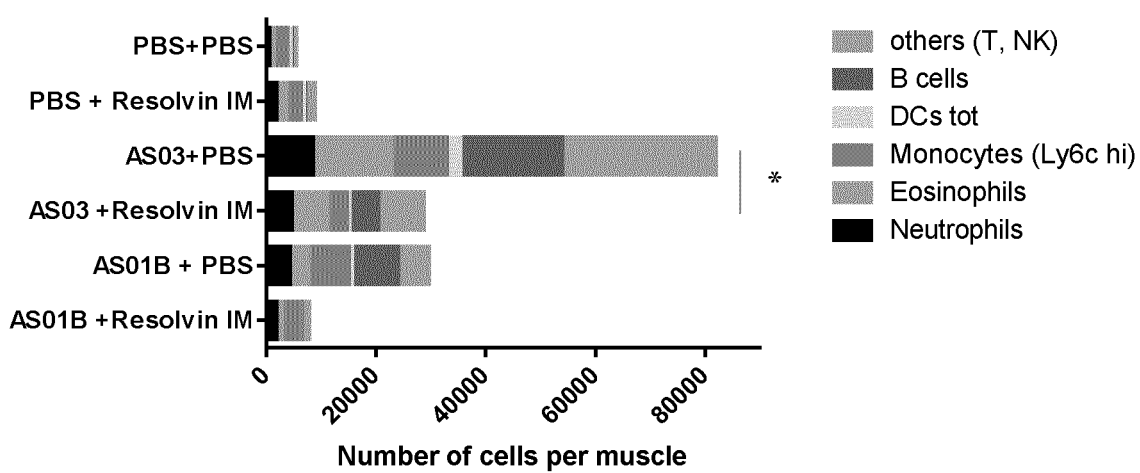
FIG. 1—Effect of Resolvin E1 (RvE1) on the local immune cells profile induced by adjuvants injection.

It is known that vaccines can sometimes be associated with reactogenicity. Reactogenicity refers to a subset of adverse events that is associated with the inflammatory response to the vaccination. The adverse events can be divided into both local (e.g. pain, swelling, erythema and induration) and systemic (e.g. fever, nausea/vomiting, diarrhoea, headaches, fatigue and myalgia). Improving vaccines by reducing their reactogenicity may improve ease of access of vaccines to specific populations, for example by reducing pain in adolescents and fever in infants. Accordingly, reduced reactogenicity may improve vaccine uptake leading to greater population coverage and therefore reducing morbidity/mortality. Moreover, an excessive inflammation may also possibly negatively affect the quality of the immune response induced by a vaccine or an immunogenic composition.

It is therefore an object of the invention to reduce the reactogenicity of vaccines. Accordingly, the present invention provides a pro-resolving mediator defined herein for use in the reduction of the reactogenicity induced by administration of a vaccine or an immunogenic composition defined herein.

Reactogenicity can be assessed directly in specific in vivo models by measuring body temperature, heart rate and/or psychomotricity with an implant, or indirectly by following biomarkers in animal blood which are indicative of the occurrence of an inflammatory response that may be associated with reactogenicity (ex: CRP, PGE2). Alternative in vitro models can also be used: they are mainly based on the activation of human cells by the formulation to test which can lead to the release of molecules with pyrogenic properties (see Schindler S. et al. "International validation of pyrogen tests based on cryopreserved human primary blood cells" *Immunol. Methods,* 2006 Oct. 20; 316 (1-2):42-51).

Resolution of the Inflammatory Response

Infection and tissue injury, or vaccination, commonly drive an acute inflammatory response, the triggering of which is responsible for the reactogenicity which may be associated with vaccines or immunogenic compositions. Said acute inflammatory response is typically divided into two distinct successive phases, namely initiation and resolution. Accordingly, the extent and duration of the acute inflammatory response can be regulated at two levels. On the one hand, by targeting compounds inhibiting the inflammatory response (antagonists) which will specifically impact the initiation phase, resulting in limitation of the duration and magnitude of the response. On the other hand, by targeting compounds which will specifically and actively promote resolution of the inflammatory response (agonists or pro-resolving mediators).

Pro-Resolving Mediators

In the sense of the present invention, by "pro-resolving mediators" it is meant compounds that promote resolution of the inflammatory response, as opposed to compounds that inhibit the inflammatory response. At the tissue and cellular level, resolution of inflammation can be defined, in a broad sense, by the rate of polymorphonuclear cell (PMN) clearance to the point when they are absent from the site of primary tissue injury and return to homeostasis. The key steps in this process include: 1) clearance of the "danger" stimuli; 2) catabolism of local survival signals and silencing of intra-cellular pro-inflammatory signalling pathways; 3) normalization of chemokine gradients and apoptosis of PMNs; and 4) efferocytosis (macrophage clearance of debris, including apoptotic neutrophils) by tissue and monocyte-derived macrophages. Pro-resolving mediators are characterized by their ability to promote/enhance one or more of any of the above steps. Some of them have also a direct action on reducing pain, by acting on terminal nerve receptors and can also accelerate wound healing and tissue repair. Mechanisms involved in the resolution of acute inflammation are described and discussed, for example, in Buckley et al. ("Proresolving Lipid Mediators and Mechanisms in the Resolution of Acute Inflammation", 2014, *Immunity* 40: 315-327) and Serhan ("Pro-resolving lipid mediators are leads for resolution physiology", 2014, *Nature* 510:92-101).

Thus, a pro-resolving mediator activity can be assessed, for example, by measuring in conditions of inflammation, for instance after vaccination, (i) the local immune cell infiltrate profile (i.e. determining the proportion of each immune cell type, such as for instance macrophages, neutrophils, eosinophils, NK cells, T cells and/or B cells in the infiltrate) and determining whether the compound to assess is capable of modulating the profile, and/or (ii) the local neutrophil apoptosis status and determining whether the compound to assess is capable of increasing the number of apoptotic neutrophils (for example by using a specific marker recognizing neutrophils and co-staining with Annexin V or Propidium iodide allowing to discriminate apoptotic cells), and/or (iii) the local inflammatory cytokines and chemokines profile and/or the presence of resolution macrophages (for example, resolution macrophages can be distinguished from inflammatory macrophages by using specific markers) and determining whether the compound to assess is capable of modulating the profile. The skilled person is familiar with the assays and techniques to use in order to evaluate any of the above. For example, after injection of a vaccine, in the absence or presence of a pro-resolving mediator, pro-resolving activity can be monitored and assessed at different time points after injection at the injection site, for example, by collecting muscles, (i) extracting immune cells, staining them with specific markers and determining the content of each cell type, for instance, by flow cytometry, and/or (ii) measuring cytokine levels within cleared homogenates obtained after homogenizing the collected muscles. Such measuring can be performed by any standard techniques of protein detection, such as for instance, Elisa assay or bead-based immunoassays allowing the simultaneous processing and measurement of multiples proteins within a single reaction, commonly referred to as Multiplex immunoassays.

At the site of injection of a vaccine for example, not only are pro-inflammatory mediators produced, but also local mediators being anti-inflammatory and local mediators being pro-resolving are produced which mediate recovery from inflammation and pain. Accordingly, anti-inflammation and pro-resolution are distinct mechanisms for the control of inflammation. The present invention relates to the use of pro-resolving mediators rather than anti-inflammatory molecules, such as for example COX2 (cyclooxygenase-2) inhibitors. The actions of pro-resolving mediators are in sharp contrast to those of currently used anti-inflammatory therapeutics (e.g. inhibitors of COX and LOX), which could be inhibitors of resolution. For instance, while anti-inflammatory mediators will block neutrophils recruitment and entry to the injury site, pro-resolving mediators will favour clearance of the neutrophils recruited and present at the injury site, by efferocytosis. Disruption of acute resolving processing will lead to uncontrolled inflammation that is implicated in the pathogenesis of many chronic diseases.

Accordingly, pro-resolving mediators have been proposed for treating pain for example, post-operative pain, arthritic pain, dental pain, lower back pain and inflammatory bowel disease (see WO 11/034887). In addition, pro-resolving mediators have been proposed for use in treating asthma/airway inflammation (WO 05/089744) and for use in treating/preventing neovascularisation and hemangiogenesis (WO 09/254873).

It has been shown that COX2 inhibitors can in fact adversely affect production of resolution mediators and can reduce the immune response to the antigen. In contrast and surprisingly, the present inventors have demonstrated that by using pro-resolving mediators, the local immune cells profile and the local cytokine profile (which underlie acute inflammation and reactogenicity) can be modulated; advantageously, the immune response to a vaccine/immunogenic composition, when using such pro-resolving mediators, is not negatively affected.

A particular family of pro-resolving mediators are lipid-derived molecules that are derived from polyunsaturated fatty acids (PUFAs). Such lipid-derived pro-resolving mediators are known to the skilled person and have been reviewed in scientific journals (see Buckley et al. "Proresolving Lipid Mediators and Mechanisms in the Resolution of Acute Inflammation", 2014, *Immunity* 40: 315-327; Serhan "Pro-resolving lipid mediators are leads for resolution physiology", 2014, *Nature* 510:92-101). Accordingly, in one embodiment, the pro-resolving mediator for use in the present invention are derived from PUFAs. The present invention contemplates in particular those derived from ω-3 PUFA eicosapentaenoic acid (EPA), for example E-type resolvins, or from ω-3 PUFA docosahexaenoic acid (DHA), for example D-type resolvins, protectins and maresins, or from ω-6 arachidonic acid (AA), for example lipoxins. Accordingly, in particular embodiments, the pro-resolving mediator for use in the present invention are derived from ω-3 PUFA eicosapentaenoic acid (EPA), ω-3 PUFA docosahexaenoic acid (DHA) or ω-6 PUFA arachidonic acid (AA). In particular, the pro-resolving mediators are selected from the group consisting of: resolvins (e.g. RvE1, RvE2, RvD1), protectins (e.g. protectin D1 (PD1), also known as neuroprotectin D1 (NPD1) when it acts in the nervous system), lipoxins (e.g. lipoxin $A_4$ ($LXA_4$)) and maresins (e.g. MaR1) or any combination of two or more thereof (e.g. RvE1, RvE2 and/or RvD1 in combination with MaR1). Resolvins can be divided into 2 types: D-type which are derived from DHA (e.g. RvD1, RvD2, RvD3 and RvD4); and E-type derived from EPA (e.g. RvE1, RvE2 and RvE3). In particular embodiments, the pro-resolving mediator used in the present invention is selected from the group consisting of: RvE1, RvE2, RvE3, RvD1, RvD2, RvD3, RvD4, MaR1, PD1/NPD1, 17-HDHA, and $LXA_4$, or a functional analogue thereof, or any combination of two or more thereof. Chemical structures of D-type resolvins (RvD1, RvD2, RvD3 and RvD4), E-type resolvins (RvE1, RvE2 and RvE3), protectins (PD1/NPD1) and maresins (MaR1) are disclosed, for example, in Buckley et al. ("Proresolving Lipid Mediators and Mechanisms in the Resolution of Acute Inflammation", 2014, *Immunity* 40: 315-327) which is incorporated herein by reference. Chemical structure of $LXA_4$ is disclosed in Serhan et al. ("Resolving inflammation: dual anti-inflammatory and pro-resolution lipid mediators", 2008, *Nat. Rev. Immunol.* 8: 349-361) which is incorporated herein by reference.

In a particular embodiment, the pro-resolving mediator is RvE1 or a functional analogue thereof. In a further particular embodiment, the pro-resolving mediator is MaR1 or a functional analogue thereof.

The pro-resolving mediators used in the present invention may be either naturally occurring or synthetic. Synthetic mimetics may be easier to produce and may offer benefits such as being chemically stable. Chemically stable mimetics of numerous pro-resolving mediators, inter alia RvE1 and RvD1, are known in the art (see Serhan & Petasis "Resolvins and Protectins in Inflammation-Resolution", 2011, *Chem Rev.* 111(10): 5922-5943; WO 05/089744; WO 09/154873 and WO 11/034887).

By "functional analogue", it is meant in the sense of the present invention for a given pro-resolving mediator, a mediator whose chemical structure is modified but retaining its ability to reduce reactogenicity and/or modulate inflammation.

Vaccine Antigens

The pro-resolving mediators of the invention described herein are used to reduce the reactogenicity of a vaccine or an immunogenic composition. Vaccines and immunogenic compositions of the invention comprise at least an antigen. By "antigen", it is meant any molecule capable of raising an immune response in a human or an animal. For instance, an antigen may be a whole-organism, a protein/polypeptide, a polysaccharide, a peptide, a nucleic acid, a protein-polysaccharide conjugate, or a hapten capable of raising an immune response in a human or an animal, each of these types of antigen, or any combination of two or more thereof, being specifically contemplated as a possible antigen in specific embodiments of the vaccines or immunogenic compositions for use in the invention. In the sense of the present invention, the terms "protein" and "polypeptide" are synonymous and interchangeable. The immune response may be raised against a pathogen, such as for example, viruses, bacteria, parasites or fungus. Accordingly, in some embodiments, the antigen in the vaccines or immunogenic compositions for use in the invention derives from an organism selected from the group consisting of: viruses, bacteria, parasites and fungus, or any combination of two or more thereof. Alternatively, the antigen may be a tumor-associated antigen, and the vaccines or immunogenic compositions of the invention may be useful for the immunotherapeutic treatment of cancers. In the sense of the present invention, "an antigen derived from an organism" encompasses, in particular, the organism as a whole (whole-organisms, such as for example a whole-virus or a whole-bacterium), or one or more molecules only from the organism. The antigen may be the naturally occurring whole-organism, and the one or more molecules, for instance, one or more polypeptides, from the organism may be isolated and purified from such naturally occurring whole-organism. Alternatively, the antigen may be artificially produced, for example, using recombinant technology or using chemical synthesis. Such recombinant antigens may be in a wild type form, i.e. their nucleotide sequence, or amino acid sequence, is identical to the sequence of the corresponding antigens derived from the naturally occurring whole-organism. Alternatively, said recombinant antigens may advantageously comprise one or more mutations, i.e. their nucleotide sequence, or amino acid sequence, comprises one or more mutations, as compared with the sequence of the corresponding wild type antigens. Whole-organisms may be live attenuated or killed/inactivated. Inactivation processes using physical and/or chemical means are known to the skilled person.

Viruses

The antigen in the vaccines or immunogenic compositions for use in the invention may derive from a virus. Accordingly, in particular embodiments, the antigen derives from a virus. In particular, the antigen may be a whole-virus. The whole virus may be live attenuated or killed/inactivated. Alternatively, the antigen may be a polypeptide derived from a virus.

Suitable viruses are from the families Orthomyxoviridae, such as for instance influenza viruses, Paramyxoviridae, such as for instance respiratory syncytial viruses (RSV), mumps virus or measles, Togaviridae, such as for instance rubella virus, Papovaviridae, such as for instance human papillomaviruses (HPV), Herpesviridae, such as for instance herpes simplex viruses (HSV), human cytomegaloviruses (HCMV), Epstein-Barr viruses (EBV), or varicella-zoster viruses (VZV), Picornaviridae, such as for instance enteroviruses, rhinoviruses, polioviruses, Flaviviridae, such as for instance Dengue viruses or hepatitis C virus (HCV), Hepadnaviridae, such as for instance hepatitis B virus (HBV), Retroviridae, such as for instance human immunodeficiency viruses (HIV), Reoviridae, such as for example rotaviruses, Rhabdoviridae, such as for instance rabies viruses, or Filoviridae, such as for example Ebola virus. In one embodiment, the antigen of the vaccines or immunogenic compositions of the invention derives from a virus selected from the group consisting of influenza virus, RSV, HPV, measles, rubella virus, mumps virus, HCMV, VZV, Dengue virus, poliovirus, HIV, HBV, Ebola virus and rotavirus, or any combination of two or more thereof.

In a particular embodiment, the antigen derives from HCMV. Suitably, the HCMV antigen is the glycoprotein gB, which may lack the transmembrane domain (as disclosed in EP0802979 B1), optionally in combination with one or more of the HCMV proteins pp65, IE1, pUL131, gL, gH, pUL128, and pUL130. Suitably, the HCMV antigen is a combination of gB, gL, gH, pUL131, pUL128 and pUL130. Alternatively, the HCMV antigen is a combination of gL, gH, pUL131, pUL128 and pUL130.

In a further particular embodiment, the antigen derives from VZV. Suitably, the VZV antigen is the glycoprotein gE, which may be deleted from its transmembrane domain, as disclosed in EP0405867 B1.

In a further particular embodiment, the antigen derives from RSV. Suitably, the RSV antigen is a polypeptide selected from the group consisting of the fusion protein (F), the attachment protein (G), the matrix protein (M2) and the nucleoprotein (N). Particularly suitable as an RSV polypeptide antigen to be included in the vaccines or immunogenic compositions in accordance with the invention are conformationally constrained F polypeptides. Conformationally constrained F polypeptides have previously been described in both the prefusion (PreF) and postfusion (PostF) conformations. Exemplary F protein antigens conformationally constrained in the prefusion conformation have been described in the art and are disclosed in detail in e.g. WO 09/079796, WO 10/149745, WO 11/008974 and WO 12/158613, each of which is incorporated herein by reference. Likewise, F protein antigens conformationally constrained in the postfusion conformation are also well known in the art and can be used in the vaccines or immunogenic compositions of the invention. Examples of postfusion conformationally constrained F protein polypeptides are disclosed in details in e.g. WO 11/008974, and Swanson et al. (*PNAS*, 2011, Vol. 108: 9619-9624), each of which is incorporated herein by reference. In particular embodiments, the vaccines or immunogenic compositions for use in the present invention comprise an antigen polypeptide derived from RSV selected from the group consisting of: F protein, preF protein, N protein and M2 protein.

In a further particular embodiment, the antigen derives from HBV. Suitably, the antigen is the Hepatitis B surface antigen (HBS).

Bacteria

The antigen in the vaccines or immunogenic compositions of the invention may derive from a bacterium. Accordingly, in particular embodiments, the antigen derives from a bacterium. In further particular embodiments, the antigen is a bacterium selected from the group consisting of: *B. pertussis*, *S. Pneumoniae*, and *N. Meningitidis*, or any combination of two or more thereof. It may be a whole-bacterium and it may be killed/inactivated or live attenuated.

Particular whole-bacterium antigens for use in the present invention are *Bordetella pertussis*. In one embodiment, the *B. pertussis* antigen is the whole-bacterium (Pw antigen), optionally in combination with tetanus toxoid (T) and/or diphtheria toxoid (D). In particular embodiments, the vaccines or immunogenic compositions of the invention comprise Pw, tetanus toxoid and diphtheria toxoid (DTPw). Pw antigen may be inactivated by several known methods, including mercury-free methods. Such methods may include heat, formaldehyde, glutaraldehyde, acetone-I, or acetone-II inactivation (see for example Gupta et al., 1987, J. Biol. Stand. 15:87; Gupta et al., 1986, Vaccine, 4:185). Methods of preparing inactivated Pw antigen suitable for use in the vaccines or immunogenic compositions of the invention are disclosed in WO 93/24148 which is incorporated herein by reference. In a particular embodiment of a Pw antigen-comprising vaccine or immunogenic composition for use in the invention, the Pw component of the composition elicits reduced reactogenicity. Reactogenicity of Pw vaccines is primarily caused by lipo-oligosaccharide ('LOS'), which is the endotoxin from the bacterial outer membrane. The lipid A part of LOS is mainly responsible for the reactogenicity. In order to produce a less reactogenic Pw antigen-containing vaccine (relative to 'traditional' Pw vaccines such as produced by the above-discussed inactivation procedures), the endotoxin can be genetically or chemically detoxified and/or extracted from the outer membrane. In particular embodiments, the *B. pertussis* antigen of the vaccine or immunogenic composition for use in the invention comprises a 'low reactogenicity' Pw antigen in which the LOS has been genetically or chemically detoxified and/or extracted. For example, the Pw antigen may be subjected to treatment with a mixture of an organic solvent, such as butanol, and water, as described in WO 06/002502 and Dias et al. (*Human Vaccines & Immunotherapeutics*, 2012, 9(2):339-348) which are incorporated herein by reference. In alternative embodiments, 'low reactogenicity' is achieved by deriving the Pw antigen from a *B. pertussis* strain genetically engineered to produce a less toxic LOS. WO 06/065139 (incorporated herein by reference) discloses genetic 3-O-deacylation and detoxification of *B. pertussis* LOS, resulting in strains comprising at least partially 3-O-deacylated LOS. The *B. pertussis* antigen of the vaccine or immunogenic composition of the invention may therefore be a Pw antigen derived from a strain of *B. pertussis* which has been engineered to express a lipid A-modifying enzyme, such as a de-O-acylase. In particular, such a strain may express the 3-O-deacylase PagL as described in WO 06/065139, as well as in Geurtsen et al. (Infection and Immunity, 2006, 74(10): 5574-5585) and Geurtsen et al. (Microbes and Infection, 2007, 9:1096-1103), all incorporated herein by reference. Alternatively or additionally, the strain from which the Pw antigen is derived may naturally, or as a result of engineering, lacks the ability to modify its lipid A phosphate groups with glucosamine, has a lipid A diglucosamine backbone substituted at the C-3' position with C10-OH or C12-OH and/or express molecular LOS species that lack a terminal heptose. Such a strain, 18-323, is disclosed in Marr et al. (*The Journal of Infectious Diseases*, 2010, 202(12): 1897-1906) (incorporated herein by reference).

Further particular bacterial antigens for use in the vaccines or immunogenic compositions in accordance with the present invention derive from *Streptococcus pneumoniae*. At least one streptococcal protein and/or at least one streptococcal capsular saccharide, optionally conjugated to a carrier protein, are suitably included as antigens in the vaccines or immunogenic compositions of the invention. Suitable protein and saccharide antigens derived from *Streptococcus pneumoniae* are described in WO 14/060385 (incorporated herein by reference). In some embodiments, the at least one *Streptococcus pneumoniae* protein is selected from the group consisting of Poly Histidine Triad family (PhtX), Choline Binding Protein Family (CbpX), CbpX truncates, LytX (autolytic enzyme) family, LytX truncates, CbpX truncate-LytX truncate chimeric proteins, PcpA (pneumococcal choline binding protein A), PspA (Pneumococcal Surface Protein A), PsaA (pneumococcal surface adhesion protein A, Sp128 (*Streptococcus pneumoniae* 128), Sp101 (*Streptococcus pneumoniae* 101), Sp130 (*Streptococcus pneumoniae* 130), SP125 (*Streptococcus pneumoniae* 125) and SP133 (*Streptococcus pneumoniae* 133). In further embodiments, the vaccines or immunogenic compositions for use in accordance with the invention comprise 1 or more (e.g. 7, 8, 9, 10, 11, 12, 13, 14, 15, 16, 17, 18, 19, 20, 21, 22 or 23) *Streptococcus pneumoniae* capsular saccharide, optionally conjugated to a carrier protein. In particular embodiments, the 1 or more *Streptococcus pneumoniae* capsular saccharide, optionally conjugated to a carrier protein, included in the vaccines or immunogenic compositions of the invention comprise saccharides derived from serotypes selected from the following serotypes 1, 2, 3, 4, 5, 6A, 6B, 7F, 8, 9N, 9V, 10A, 11A, 12F, 14, 15B, 17F, 18C, 19A, 19F, 20, 22F, 23F and 33F. For example, a 7-valent vaccine or immunogenic composition may comprise saccharides from serotypes 4, 6B, 9V, 14, 18C, 19F and 23F. A 10-valent vaccine or immunogenic composition may comprise saccharides derived from the same 7 serotypes and further comprise saccharides from serotypes 1, 5 and 7F. A 12-valent vaccine or immunogenic composition may comprise saccharides derived from the same 10 serotypes and further comprise saccharides derived from serotypes 6A and 19A. A 13-valent vaccine or immunogenic composition may comprise the same 12 serotypes and further comprise serotype 3. A 15-valent vaccine or immunogenic composition may comprise saccharides derived from the same 13 serotypes and further comprise saccharides derived from serotypes 22F and 33F. Further saccharide antigens, for example a 23-valent (such as serotypes 1, 2, 3, 4, 5, 6B, 7F, 8, 9N, 9V, 10A, 11A, 12F, 14, 15B, 17F, 18C, 19A, 19F, 20, 22F, 23F and 33F), are also contemplated as antigens in the vaccines or immunogenic compositions for use in the invention. The term "saccharide" may indicate polysaccharide or oligosaccharide and includes both. Polysaccharides are isolated from bacteria and may be sized to some degree by known methods (see for example EP0497524 B1 and EP0497525 incorporated herein by reference) and optionally by microfluidisation. Polysaccharides can be sized in order to reduce viscosity in polysaccharide samples and/or to improve filterability for conjugated products. The terms "conjugate" relate to a capsular saccharide covalently bonded to a carrier protein. The carrier protein may be any peptide or protein. Suitable carrier proteins are described in WO 14/060385 (incorporated herein by reference). The carrier protein may be tetanus toxoid (TT), tetanus toxoid fragment C, non-toxic mutants of tetanus toxin, diphtheria toxoid (DT), CRM197, other non-toxic mutants of diphtheria toxin, such as CRM176, CRM228, CRM 45; CRM 9, CRM 45, CRM102, CRM103 and CRM107 (where CRM stands for Cross Reacting Material), pneumococcal pneumolysin, OMPC (outer membrane protein C), heat shock proteins, pertussis proteins, cytokines, lymphokines, growth factors or hormones, artificial proteins comprising multiple human CD4+ T cell epitopes from various pathogen derived antigens, such as N19 protein, pneumococcal surface protein PspA, iron uptake proteins, toxin A or B of *C. difficile, H. influenzae* Protein, pneumococcal PhtA (poly histidine triad protein A), pneumococcal PhtD (poly histidine triad protein D, pneumococcal PhtB (poly histidine triad protein B), or PhtE (poly histidine triad protein E). In one embodiment the at least one *Streptococcus pneumoniae* capsular saccharide conjugate is conjugated to a carrier protein selected from the group consisting of tetanus toxoid (TT), fragment C of TT, diphtheria toxoid, CRM197 (cross reacting material 197), detoxified pneumolysin, protein D (from *H. influenzae*), PhtD, PhtDE and N19. The saccharide may be linked to the carrier protein by any known method.

Further particular bacterial antigens for use in the present invention are derived from *Neisseria meningitidis*. In some embodiments, than antigen of the vaccines or immunogenic compositions for use in the invention is a *N. meningitidis* capsular saccharide from a serogroup selected from the group consisting of: serogroup A (MenA), serogroup C (MenC), serogroup Y (MenY), and serogroup W-135 (MenW), or any combination of two or more thereof, optionally conjugated to a carrier protein. Indeed, these saccharides may suitably be conjugated to any of the carrier protein described above in relation to streptococcal saccharides. In some embodiments, the vaccine or immunogenic compositions of the invention comprise a *N. meningitidis* serogroup A capsular saccharide (MenA), *N. meningitidis* serogroup C capsular saccharide (MenC), *N. meningitidis* serogroup Y capsular saccharide (MenY), and *N. meningitidis* serogroup W-135 capsular saccharide (MenW), optionally conjugated to the carrier protein CRM197 or the carrier protein TT.

Further particular bacterial antigens derived from *Neisseria meningitidis* for use in the present invention are derived from *N. meningitidis* serogroup B ("MenB"). Suitable antigens for eliciting anti-MenB responses include polypeptides, lipo-oligosaccharide and/or membrane vesicles. Vaccines or immunogenic compositions of the invention may include one or more serogroup B meningococcal polypeptide antigen(s). In some embodiments, the antigen is a N. *Meningitidis* serogroup B polypeptide selected from the group consisting of: NadA protein (also known as protein '961'), NHBA protein (also known as protein '287'), fHBP protein (also known as protein '741'), GNA1030 protein (also known as protein '953'), and GNA2091 protein (also known as protein '936'), or any combination of two or more thereof, optionally in combination with a *N. meningitidis* serogroup B-derived OMV. These antigens will usefully be present as purified polypeptides, e.g. recombinant polypeptides. Suitable forms of these antigens are disclosed in WO 04/032958 incorporated herein by reference. The five antigens may be present in the composition as five separate proteins, or suitably at least two of the antigens are expressed as a single polypeptide chain (a 'hybrid' protein) e.g. such that the five antigens form fewer than five polypeptides, as described in WO 04/032958. In some embodiments, vaccines or immunogenic compositions of the invention comprise at least NadA protein, NHBA protein, fHBP protein, GNA1030 protein and GNA2091 protein. In particular embodiments, vaccines or immunogenic compositions of the invention comprise SEQ ID NO:2, SEQ ID NO:7 and SEQ ID NO:8 as disclosed in WO 04/032958 incorporated herein by reference. In further particular embodiments, such vaccines or immunogenic compositions of the invention additionally comprise an *N. meningitidis* serogroup B-derived OMV, as described below.

Further particular bacterial antigens are outer membrane vesicles (OMV). These include any proteo-liposomic vesicle obtained by disruption of or blebbling from an outer membrane to form vesicles therefrom that include protein components of the outer membrane. Gram-negative bacteria, such as *Neisseria* secrete OMV during active growth. The primary immunogenic components of the OMV are the outer membrane proteins (OMPs) and the membrane-bound lipopolysaccharides (LPS). OMVs may be prepared from any Gram-negative bacterium, including pathogenic Neisserial bacteria such as *Neisseria gonorrhoea* and *Neisseria meningitidis*. The OMV approach is particularly useful for *Neisseria meningitidis* serogroup B, as its polysaccharide capsule is poorly immunogenic. Accordingly, in some embodiments, vaccines or immunogenic compositions of the invention comprise an OMV derived from a *N. meningitidis* serogroup B strain, optionally in combination with any of the above-described serogroup B meningococcal polypeptide antigens. OMVs are prepared artificially from bacteria, and may be prepared using detergent treatment (e.g. with deoxycholate), or by non-detergent means, as described in WO 12/020326, for example, which is incorporated herein by reference.

Parasites

The antigen in the vaccines or immunogenic compositions of the invention may derive from parasites. Suitably, the antigen may derive from parasites causing Malaria. Accordingly, in some embodiments, the antigen in vaccines or immunogenic compositions for use in the invention is derived from parasites that cause Malaria, such as for example, *Plasmodium falciparum* or *Plasmodium vivax*. Suitably, the *Plasmodium falciparum*-derived antigen is RTS,S. As disclosed in WO 93/10152 (incorporated herein by reference), RTS, S is a hybrid protein consisting of the C-terminal portion of the circumsporozoite (CS) protein of *Plasmodium falciparum* linked via four amino acids of the preS2 portion of Hepatitis B surface antigen to the surface (S) antigen of Hepatitis B virus.

Tumor-Associated Antigens

The antigen in the vaccines or immunogenic compositions of the invention may be a tumor-associated antigen. Suitably, the antigen may be a tumor rejection antigen, such as those for prostate, breast, colorectal, lung, pancreatic, renal or melanoma cancers. Exemplary, non-limiting, antigens include MAGE 1, 3 and MAGE 4 or other MAGE antigens, such as disclosed in WO 99/40188.

Nucleic Acid Immunisation

Self-Replicating RNA

Nucleic acid immunisation may be achieved by delivering a self-replicating RNA (or self-amplifying RNA) encapsulated within and/or adsorbed to a small particle. The RNA encodes a polypeptide antigen of interest, and the particle may deliver this RNA by mimicking the delivery function of a natural virus. After in vivo administration of the particles, RNA is released from the particles and is translated inside a cell to provide the antigen in situ.

Any of the polypeptide antigens described above as suitable to be included in the vaccines or immunogenic compositions in accordance with the invention may be expressed in the form of a self-replicating RNA molecule encoding said antigen, as described in WO 12/006376 which is incorporated herein by reference. Accordingly, in particular embodiments where antigens in the vaccines or immunogenic compositions for use in the invention are polypeptides, such polypeptides are encoded by a self-replicating RNA. In such cases, said self-replicating RNA is suitably coupled with a delivery system, in particular lipid-based delivery systems, such as a cationic nanoemulsion (CNE), or a liposome. Suitably, when the lipid-based system is a CNE the self-replicating RNA is adsorbed to the outer surface of the CNE, while when said lipid-based system is a liposome the self-amplifying RNA is encapsulated into the liposome.

By "self-replicating RNA molecule" (or "self-amplifying RNA"), it is meant that, when delivered to a vertebrate cell, even without any proteins, the molecule leads to the production of multiple daughter RNAs by transcription from itself as explained in WO 12/006376, which ultimately results into the expression of the encoded antigen, becoming a major polypeptide of the cells.

One suitable system for achieving self-replication in this manner is to use an alphavirus-based replicon, as further described in WO 12/006376. Suitably, said replicon encodes (i) a RNA-dependent RNA polymerase which can transcribe RNA from the self-replicating RNA molecule and (ii) an antigen of interest. The polymerase can be an alphavirus replicase e.g. comprising one or more alphavirus proteins nsP1, nsP2, nsP3 and nsP4. Appropriate features of self-replicating RNA molecules and methods for preparing them are also described in WO 12/006376.

In some embodiments, the vaccines or immunogenic compositions for use in the present invention comprise a liposome and a self-replicating RNA encoding any of the polypeptide antigens herein described encapsulated into the liposome. In further embodiments, the vaccines or immunogenic compositions for use in the present invention comprise a CNE and a self-replicating RNA encoding any of the polypeptide antigens herein described adsorbed to the outer surface of the CNE. In particular embodiments, the self-replicating RNA molecule encodes polypeptide antigens derived from the group consisting of: HCMV, RSV and HIV.

Exemplary CNE for use in the present invention, as well as methods for their preparation are disclosed in WO 12/006380 which is incorporated herein by reference.

Various amphiphilic lipids can form bilayers in an aqueous environment to encapsulate a RNA-containing aqueous core as a liposome. These lipids can have an anionic, cationic or zwitterionic hydrophilic head group. Some phospholipids are anionic whereas others are zwitterionic and others are cationic. Suitable classes of phospholipids include, but are not limited to, phosphatidylethanolamines, phosphatidylcholines, phosphatidylserines, and phosphatidyl-glycerols. Useful cationic lipids include, but are not limited to, dioleoyl trimethylammonium propane (DOTAP), 1,2-distearyloxy-N,N-dimethyl-3-aminopropane (DSDMA), 1,2-dioleyloxy-N,N dimethyl-3-aminopropane (DODMA), 1,2-dilinoleyloxy-N,N-dimethyl-3-aminopropane (DLinDMA), 1,2-dilinolenyloxy-N,N-dimethyl-3-aminopropane (DLenDMA). Further useful cationic lipids are described in WO 15/095340, for example the lipids as claimed in any of claims 1 to 8 of WO 15/095340 incorporated herein by reference. Zwitterionic lipids include, but are not limited to, acyl zwitterionic lipids and ether zwitterionic lipids. Examples of useful zwitterionic lipids are DPPC, DOPC and dodecylphosphocholine. Liposomal particles of the invention can be formed from a single lipid or from a mixture of lipids. A mixture may comprise (i) a mixture of anionic lipids, (ii) a mixture of cationic lipids, (iii) a mixture of zwitterionic lipids, (iv) a mixture of anionic lipids and cationic lipids, (v) a mixture of anionic lipids and zwitterionic lipids, (vi) a mixture of zwitterionic lipids and cationic lipids or (vii) a mixture of anionic lipids, cationic lipids and zwitterionic lipids. Where a mixture of lipids is used, not all of the component lipids in the mixture need to be amphiphilic e.g. one or more amphiphilic lipids can be mixed with cholesterol. The hydrophilic portion of a lipid can be PEGylated (i.e. modified by covalent attachment of a polyethylene glycol). This modification can increase stability and prevent non-specific adsorption of the liposomes. Liposomal particles are usually divided into three groups: multilamellar vesicles (MLV); small unilamellar vesicles (SUV); and large unilamellar vesicles (LUV). MLVs have multiple bilayers in each vesicle, forming several separate aqueous compartments. SUVs and LUVs have a single bilayer encapsulating an aqueous core; SUVs typically have a diameter 50 nm, and LUVs have a diameter >50 nm. Liposomal particles useful in this aspect of the invention are ideally LUVs with a diameter in the range of 50-220 nm. Techniques for preparing suitable liposomes are well known in the art. One useful method is described in Jeffs et al. (*Pharmaceutical Research,* 2005, 22(3): 362-372) and involves mixing (i) an ethanolic solution of the lipids (ii) an aqueous solution of the nucleic acid and (iii) buffer, followed by mixing, equilibration, dilution and purification.

Viral Vectors

Alternatively, nucleic acid immunisation may be achieved by using a replicating or replication-defective vector, such as a viral vector. Numerous viral vectors suitable for introducing nucleic acids encoding antigens of interest into a subject are known in the art, and include both DNA and RNA viruses. Suitable examples are for instance: adenovirus vectors (replication or replication deficient), pox virus vectors, including vaccinia virus vectors, such as modified vaccinia Ankara virus (MVA), NYVAC, avipox vectors, canarypox (ALVAC) and fowl pox virus (FPV), Alphavirus vectors (such as Sindbis virus, Semlike Forest virus, Ross River virus, and Venezuelan equine encephalitis virus) and chimeras and replicons thereof, herpes virus vectors (e.g. cytomegalovirus-derived vectors), arena virus vectors, such as lymphocytic choriomeningitis virus (LCMV) retrovirus, lentivirus, viral like particles, and many others. In one embodiment, the polypeptide antigen in the vaccines or immunogenic compositions for use in the present invention is encoded by an adenoviral vector. In particular embodiments, the polypeptide antigen encoded by an adenoviral vector derives from HIV, Malaria, Ebola or RSV. The production and use of adenovirus vectors are well known to those of ordinary skill in the art. Suitable examples of disclosure of the design, production and use of adenovirus vectors can be found, for instance, in WO 05/071093, and WO 10/086189 which are incorporated herein by reference. Adenoviral vectors for use in the present invention may be derived from a range of mammalian hosts. Adenoviral vectors may be derived from a human adenovirus. Examples of such human-derived adenoviruses are Ad1, Ad2, Ad4, Ad5, Ad6, Ad11, Ad24, Ad34, Ad35, particularly Ad5, Ad11 and Ad35.

Alternatively, adenoviral vectors may be derived from a non-human primate adenovirus e.g. a chimpanzee adenovirus, such as one selected from serotypes ChAd3, ChAd63, ChAd83, ChAd155, Pan5, Pan6, Pan7 and Pan9. Specifically, the virus may be a non-human adenovirus, such as a simian adenovirus and in particular a chimpanzee adenovirus such as ChAd155, Pan 5, 6, 7 or 9. Examples of such strains are described in WO 03/000283 which is incorporated herein by reference and are available from the American Type Culture Collection, 10801 University Boulevard, Manassas, Va. 20110-2209, and other sources. Desirable chimpanzee adenovirus strains include Pan 5 [ATCC VR-591], Pan 6 [ATCC VR-592], and Pan 7 [ATCC VR-593].

The adenoviral vectors for use in the present invention may be derived from replication-defective adenovirus, for example, comprising a functional E1 deletion. Adenoviral vectors for use in the present invention include PanAd3 (WO 10/086189) and ChAd155 (GB1510357.5). In some embodiments, the antigen of the vaccines or immunogenic compositions for use in the invention is recombinantly expressed in the adenoviral vector ChAd155. In particular embodiments, the adenoviral vector ChAd155 encodes at least an antigen derived from respiratory syncytial virus (RSV), in particular any of the above-described RSV polypeptide antigen. The adenoviral vectors can be produced on any suitable cell line in which the virus is capable of replication. Without limitation, such a cell line may be HeLa [ATCC Accession No. CCL 2], A549 [ATCC Accession No. CCL 185], HEK 293, KB [CCL 17], Detroit [e.g., Detroit 510, CCL 72] and WI-38 [CCL 75] cells, among others.

Adjuvants

Vaccines and immunogenic compositions of the invention may also comprise an adjuvant in addition to the antigen. Adjuvants are used in vaccines in order to enhance and modulate the immune response to the antigen. However, adjuvants can result in increased reactogenicity and in these particular embodiments, the vaccines and immunogenic compositions of the invention comprise an adjuvant. The adjuvants described herein below may be combined with any of the antigen(s) herein described above.

The adjuvant may be any adjuvant known to the skilled person, but adjuvants include (but are not limited to) oil-in-water emulsions containing squalene (for example MF59 or AS03), liposomes, saponins, TLR2 agonists, TLR3 agonists, TLR4 agonists, TLR5 agonists, TLR6 agonists, TLR7 agonists, TLR8 agonists, TLR9 agonists, aluminium salts, nanoparticles, microparticles, ISCOMS, calcium fluoride and organic compound composites or combinations thereof.

Oil-in-Water Emulsions

In an embodiment of the present invention, there is provided a vaccine or immunogenic composition for use in the invention comprising an oil-in-water emulsion. Oil-in-water emulsions of the present invention comprise a metabolisable oil and an emulsifying agent. In order for any oil-in-water composition to be suitable for human administration, the oil phase of the emulsion system has to comprise a metabolisable oil. The meaning of the term metabolisable oil is well known in the art. Metabolisable can be defined as "being capable of being transformed by metabolism" (Dorland's Illustrated Medical Dictionary, W.B. Sanders Company, 25th edition, 1974). A particularly suitable metabolisable oil is squalene. Squalene (2,6,10,15,19,23-Hexamethyl-2,6,10,14,18,22-tetracosahexaene) is an unsaturated oil which is found in large quantities in shark-liver oil, and in lower quantities in olive oil, wheat germ oil, rice bran oil, and yeast, and is a particularly preferred oil for use in an oil-in-water emulsion of the invention. Squalene is a metabolisable oil by virtue of the fact that it is an intermediate in the biosynthesis of cholesterol (Merck index, 10th Edition, entry no. 8619). In some embodiments, wherein the vaccines or immunogenic compositions of the invention comprise an oil-in-water emulsion, the metabolisable oil is present in the vaccine or in the immunogenic composition in an amount of 0.5% to 10% (v/v) of the total volume of the composition. The oil-in-water emulsion further comprises an emulsifying agent. The emulsifying agent may suitably be polyoxyethylene sorbitan monooleate (POLYSORBATE 80). Further, said emulsifying agent is suitably present in the vaccine or immunogenic composition in an amount of 0.125 to 4% (v/v) of the total volume of the composition. The oil-in-water emulsion may optionally comprise a tocol. Tocols are well known in the art and are described in EP0382271 B1. Suitably, the tocol may be alpha-tocopherol or a derivative thereof such as alpha-tocopherol succinate (also known as vitamin E succinate). Said tocol is suitably present in the adjuvant composition in an amount of 0.25% to 10% (v/v) of the total volume of the immunogenic composition. The oil-in-water emulsion may also optionally comprise sorbitan trioleate (SPAN 85).

The method of producing oil-in-water emulsions is well known to the person skilled in the art. Commonly, the method comprises mixing the oil phase (optionally comprising a tocol) with a surfactant such as a PBS/TWEEN80™ solution, followed by homogenisation using a homogenizer, it would be clear to a person skilled in the art that a method comprising passing the mixture twice through a syringe needle would be suitable for homogenising small volumes of liquid. Equally, the emulsification process in microfluidiser (M110S Microfluidics machine, maximum of 50 passes, for a period of 2 minutes at maximum pressure input of 6 bar (output pressure of about 850 bar)) could be adapted by the person skilled in the art to produce smaller or larger volumes of emulsion. The adaptation could be achieved by routine experimentation comprising the measurement of the resultant emulsion until a preparation was achieved with oil droplets of the required diameter.

In an oil-in-water emulsion, the oil and emulsifier should be in an aqueous carrier. The aqueous carrier may be, for example, phosphate buffered saline or citrate.

In particular, the oil-in-water emulsion systems used in the present invention have a small oil droplet size in the sub-micron range. Suitably the droplet sizes will be in the range 120 to 750 nm, more particularly sizes from 120 to 600 nm in diameter. Even more particularly, the oil-in water emulsion contains oil droplets of which at least 70% by intensity are less than 500 nm in diameter, more particular at least 80% by intensity are less than 300 nm in diameter, more particular at least 90% by intensity are in the range of 120 to 200 nm in diameter.

The oil droplet size, i.e. diameter, according to the present invention is given by intensity. There are several ways of determining the diameter of the oil droplet size by intensity. Intensity is measured by use of a sizing instrument, suitably by dynamic light scattering such as the Malvern Zetasizer 4000 or preferably the Malvern Zetasizer 3000HS. A first possibility is to determine the z average diameter ZAD by dynamic light scattering (PCS-Photon correlation spectroscopy); this method additionally gives the polydispersity index (PDI), and both the ZAD and PDI are calculated with the cumulants algorithm. These values do not require the knowledge of the particle refractive index. A second mean is to calculate the diameter of the oil droplet by determining the whole particle size distribution by another algorithm, either the Contin, or NNLS, or the automatic "Malvern" one (the default algorithm provided for by the sizing instrument). Most of the time, as the particle refractive index of a complex composition is unknown, only the intensity distribution is taken into consideration, and if necessary the intensity mean originating from this distribution.

ISCOMs

In some embodiments of the present invention, there are provided vaccines or immunogenic compositions of the invention comprising ISCOMs. ISCOMs are well known in the art (see Kersten & Crommelin, 1995, *Biochimica et Biophysica Acta* 1241: 117-138). ISCOMs comprise a saponin, cholesterol and phospholipids and form an open-cage-like structure of typically 40 nm in size. ISCOMs result from the interaction of saponins, cholesterol and further phospholipids. A typical reaction mixture for the preparation of ISCOM is 5 mg/ml saponin and 1 mg/ml each for cholesterol and phospholipid. Phospholipids suitable for use in ISCOMs include, but are not limited, to phosphocholine (didecanoyl-L-α-phosphatidylcholine [DDPC], dilauroylphosphatidylcholine [DLPC], dimyristoylphosphatidylcholine [DMPC], dipalmitoyl phosphatidylcholine [DPPC], Distearoyl phosphatidylcholine [DSPC], Dioleoyl phosphatidylcholine [DOPC], 1-palmitoyl, 2-oleoylphosphatidylcholine [POPC], Dielaidoyl phosphatidylcholine [DEPC]), phosphoglycerol (1,2-Dimyristoyl-sn-glycero-3-phosphoglycerol [DMPG], 1,2-dipalmitoyl-sn-glycero-3-phosphoglycerol [DPPG], 1,2-distearoyl-sn-glycero-3-phosphoglycerol [DSPG], 1-palmitoyl-2-oleoyl-sn-glycero-3-phosphoglycerol [POPG]), phosphatidic acid (1,2-dimyristoyl-sn-glycero-3-phosphatidic acid [DMPA], dipalmitoyl phosphatidic acid [DPPA], distearoyl-phosphatidic acid [DSPA]), phosphoethanolamine (1,2-dimyristoyl-sn-glycero-3-phosphoethanolamine [DMPE], 1,2-Dipalmitoyl-sn-glycero-3-phosphoethanolamine [DPPE], 1,2-distearoyl-sn-glycero-3-phosphoethanolamine DSPE 1,2-Dioleoyl-sn-Glycero-3-Phosphoethanolamine [DOPE]), phosphoserine, polyethylene glycol [PEG] phospholipid (mPEG-phospholipid, polyglycerin-phospholipid, functionalized-phospholipid, terminal activated-phospholipid). In particular embodiments, ISCOMs comprise 1-palmitoyl-2-oleoyl-glycero-3-phosphoethanolamine. In further particular embodiments, highly purified phosphatidylcholine is used and can be selected from the group consisting of: Phosphatidylcholine (from egg), Phosphatidylcholine Hydrogenated (from egg) Phosphatidylcholine (from soy), Phosphatidylcholine Hydrogenated (from soy). In further particular embodiments, ISCOMs comprise phosphatidylethanolamine [POPE] or a derivative thereof. A number of saponins are suitable for use in ISCOMs. The adjuvant and haemolytic activity of individual saponins has been extensively studied in the art. For example, Quil A (derived from the bark of the South American tree *Quillaja Saponaria Molina*), and fractions thereof, are described in U.S. Pat. No. 5,057,540 and "Saponins as vaccine adjuvants", Kensil, C. R., *Crit Rev Ther Drug Carrier Syst*, 1996, 12 (1-2):1-55; and EP0362279 B1. ISCOMs comprising fractions of Quil A have been used in the manufacture of vaccines (EP0109942 B1). These structures have been reported to have adjuvant activity (EP0109942 B1; WO 96/11711). Fractions of QuilA, derivatives of QuilA and/or combinations thereof are suitable saponin preparations for use in ISCOMs. The haemolytic saponins QS21 and QS17 (HPLC purified fractions of Quil A) have been described as potent adjuvants, and the method of their production is disclosed in U.S. Pat. No. 5,057,540 and EP0362279 B1. Also described in these references is the use of QS7 (a non-haemolytic fraction of Quil-A) which acts as a potent adjuvant for systemic vaccines. Use of QS21 is further described in Kensil et al. (1991. J. Immunology vol 146, 431-437). Combinations of QS21 and polysorbate or cyclodextrin are also known (WO 99/10008). Particulate adjuvant systems comprising fractions of QuilA, such as QS21 and QS7 are described in WO 96/33739 and WO 96/11711 and these are incorporated herein. Other particular QuilA fractions designated QH-A, QH-B, QH-C and a mixture of QH-A and QH-C designated QH-703 are disclosed in WO 96/011711 in the form of ISCOMs and are incorporated herein.

Microparticles

In some embodiments of the present invention, there is provided a vaccine or immunogenic composition of the invention comprising microparticles. Microparticles, compositions comprising microparticles, and methods of producing microparticles are well known in the art (see Singh et al. [2007 *Expert Rev. Vaccines* 6(5): 797-808] and WO 98/033487). The term "microparticle" as used herein, refers to a particle of about 10 nm to about 10,000 μm in diameter or length, derived from polymeric materials which have a variety of molecular weights and, in the case of the copolymers such as PLG, a variety of lactide:glycolide ratios. In particular, the microparticles will be of a diameter that permits parenteral administration without occluding needles and capillaries. Microparticles are also known as microspheres. Microparticle size is readily determined by techniques well known in the art, such as photon correlation spectroscopy, laser diffractometry and/or scanning electron microscopy. Microparticles for use herein will be formed from materials that are sterilizable, non-toxic and biodegradable. Such materials include, without limitation, poly (a-hydroxy acid), polyhydroxybutyric acid, polycaprolactone, polyorthoester, polyanhydride.

Liposomes

In some embodiments of the present invention, there is provided a vaccine or immunogenic composition of the invention comprising liposomes. The term "liposomes" generally refers to uni- or multilamellar (particularly 2, 3, 4, 5, 6, 7, 8, 9, or 10 lamellar depending on the number of lipid membranes formed) lipid structures enclosing an aqueous interior. Liposomes and liposome formulations are well known in the art. Lipids, which are capable of forming liposomes, include all substances having fatty or fat-like properties. Lipids which can make up the lipids in the liposomes can be selected from the group comprising of glycerides, glycerophospholipides, glycerophosphinolipids, glycerophosphonolipids, sulfolipids, sphingolipids, phospholipids, isoprenolides, steroids, stearines, sterols, archeolipids, synthetic cationic lipids and carbohydrate containing lipids. Liposome size may vary from 30 nm to several μm depending on the phospholipid composition and the method used for their preparation. In particular embodiments of the invention, the liposome size will be in the range of 50 nm to 500 nm, and in further embodiments, 50 nm to 200 nm. Dynamic laser light scattering is a method used to measure the size of liposomes well known to those skilled in the art. The liposomes suitably contain a neutral lipid, for example phosphatidylcholine, which is suitably non-crystalline at room temperature, for example egg yolk phosphatidylcholine, dioleoyl phosphatidylcholine (DOPC) or dilauryl phosphatidylcholine. In a particular embodiment, the liposomes of the present invention contain DOPC. The liposomes may also contain a charged lipid which increases the stability of the liposome-saponin structure for liposomes composed of saturated lipids. In these cases the amount of charged lipid is suitably 1 to 20% (w/w), preferably 5 to 10%. The ratio of sterol to phospholipid is 1 to 50% (mol/mol), suitably 20 to 25% (mol/mol).

Saponins

In some embodiments of the invention, the vaccine or immunogenic composition of the invention comprises a saponin. A particularly suitable saponin for use in the present invention is Quil A and its derivatives. Quil A is a saponin preparation isolated from the South American tree *Quillaja Saponaria Molina* and was first described by Dalsgaard et al. in 1974 ("Saponin adjuvants", *Archiv. für die gesamte Virusforschung*, Vol. 44, Springer Verlag, Berlin, p 243-254) to have adjuvant activity. Purified fragments of Quil A have been isolated by HPLC which retain adjuvant activity without the toxicity associated with Quil A (EP0362278), for example QS7 and QS21 (also known as QA7 and QA21). QS-21 is a natural saponin derived from the bark of *Quillaja saponaria Molina*, which induces CD8+ cytotoxic T cells (CTLs), Th1 cells and a predominant IgG2a antibody response and is a particular saponin in the context of the present invention. The saponin adjuvant within the immunogenic compositions of the invention in particular are immunologically active fractions of Quil A, such as QS-7 or QS-21, suitably QS-21. In particular embodiments, the vaccines immunogenic compositions of the invention contain the immunologically active saponin fraction in substantially pure form. In particular, the vaccines or immunogenic compositions of the invention contain QS21 in substantially pure form, that is to say, the QS21 is at least 75%, 80%, 85%, 90% pure, for example at least 95% pure, or at least 98% pure.

In a particular embodiment, QS21 is with an exogenous sterol, such as cholesterol for example. Suitable sterols include β-sitosterol, stigmasterol, ergosterol, ergocalciferol and cholesterol. In a further particular embodiment, the adjuvant composition comprises cholesterol as sterol. These sterols are well known in the art, for example cholesterol is disclosed in the Merck Index, 11th Edition, page 341, as a naturally occurring sterol found in animal fat.

In one embodiment, the liposomes of the invention that comprise a saponin suitably contain a neutral lipid, for example phosphatidylcholine, which is suitably non-crystalline at room temperature, for example egg yolk phosphatidylcholine, dioleoyl phosphatidylcholine (DOPC) or dilauryl phosphatidylcholine. The liposomes may also contain a charged lipid which increases the stability of the liposome-QS21 structure for liposomes composed of saturated lipids. In these cases the amount of charged lipid is suitably 1 to 20% (w/w), particularly 5 to 10% (w/w). The ratio of sterol to phospholipid is 1 to 50% (mol/mol), suitably 20 to 25% (mol/mol).

Where the active saponin fraction is QS21, the ratio of QS21:sterol will typically be in the order of 1:100 to 1:1 (w/w), suitably between 1:10 to 1:1 (w/w), and preferably 1:5 to 1:1 (w/w). Suitably, excess sterol is present, the ratio of QS21:sterol being at least 1:2 (w/w). In one embodiment, the ratio of QS21:sterol is 1:5 (w/w). The sterol is suitably cholesterol.

Other useful saponins are derived from the plants *Aesculus hippocastanum* or *Gyophilla struthium*. Other saponins which have been described in the literature include Escin, which has been described in the Merck index (12th Edition: entry 3737) as a mixture of saponins occurring in the seed of the horse chestnut tree, Lat: *Aesculus hippocastanum*. Its isolation is described by chromatography and purification (Fiedler, *Arzneimittel-Forsch.* 4, 213 (1953)), and by ion-exchange resins (Erbring et al., U.S. Pat. No. 3,238,190). Fractions of Escin have been purified and shown to be biologically active (Yoshikawa et al., 1996, *Chem Pharm Bull* (Tokyo), 44(8): 1454-1464). Sapoalbin from *Gypsophilla struthium* (R. Vochten et al., 1968, *J. Pharm. Belg.* 42: p 213-226) has also been described in relation to ISCOM production for example.

A saponin, such as QS21, can be used at amounts between 1 and 100 μg per human dose of the adjuvant composition. QS21 may be used at a level of about 50 μg, for example between 40 to 60 μg, suitably between 45 to 55 μg or between 49 and 51 μg or 50 μg. In a further embodiment, the human dose of the adjuvant composition comprises QS21 at a level of about 25 μg, for example between 20 to 30 μg, suitably between 21 to 29 μg or between 22 to 28 μg or between 28 and 27 μg or between 24 and 26 μg, or 25 μg.

TLR4 Agonist

In some embodiments, the vaccine or immunogenic composition of the invention comprises a TLR4 agonist. By "TLR agonist" it is meant a component which is capable of causing a signalling response through a TLR signalling pathway, either as a direct ligand or indirectly through generation of endogenous or exogenous ligand (Sabroe et al, 2003, JI p 1630-5). A TLR4 agonist is capable of causing a signalling response through a TLR-4 signalling pathway. A suitable example of a TLR-4 agonist is a lipopolysaccharide, suitably a non-toxic derivative of lipid A, particularly monophosphoryl lipid A or more particularly 3-Deacylated monophoshoryl lipid A (3D-MPL).

3D-MPL is sold under the name MPL by GlaxoSmithKline Biologicals and is referred throughout the document as MPL or 3D-MPL. See, for example, U.S. Pat. Nos. 4,436,727; 4,877,611; 4,866,034 and 4,912,094. 3D-MPL primarily promotes CD4+ T cell responses with an IFN-γ (Th1) phenotype. 3D-MPL can be produced according to the methods disclosed in GB 2 220 211 A. Chemically, it is a mixture of 3-deacylated monophosphoryl lipid A with 4, 5 or 6 acylated chains. In the compositions of the present invention, small particle 3D-MPL may be used to prepare the aqueous adjuvant composition. Small particle 3D-MPL has a particle size such that it may be sterile-filtered through a 0.22 μm filter. Such preparations are described in WO 94/21292. Preferably, powdered 3D-MPL is used to prepare the aqueous adjuvant compositions of the present invention.

Other TLR-4 agonists which can be used are alkyl glucosaminide phosphates (AGPs) such as those disclosed in WO 98/50399 or U.S. Pat. No. 6,303,347 (processes for preparation of AGPs are also disclosed), suitably RC527 or RC529 or pharmaceutically acceptable salts of AGPs as disclosed in U.S. Pat. No. 6,764,840.

Other suitable TLR-4 agonists are as described in WO 03/011223 and in WO 03/099195, such as compound I, compound II and compound III disclosed on pages 4-5 of WO 03/011223 or on pages 3 to 4 of WO 03/099195 and in particular those compounds disclosed in WO 03/011223, as ER803022, ER803058, ER803732, ER804053, ER804057m ER804058, ER804059, ER804442, ER804680 and ER804764. For example, one suitable TLR-4 agonist is ER804057.

A TLR-4 agonist, such as a lipopolysaccharide, such as 3D-MPL, can be used at amounts between 1 and 100 μg per human dose of the adjuvant composition. 3D-MPL may be used at a level of about 50 μg, for example between 40 to 60 μg, suitably between 45 to 55 μg or between 49 to 51 μg or 50 μg. In a further embodiment, the human dose of the adjuvant composition comprises 3D-MPL at a level of about 25 μg, for example between 20 to 30 μg, suitably between 21 to 29 μg or between 22 to 28 μg or between 28 to 27 μg or between 24 to 26 μg, or 25 μg.

Synthetic derivatives of lipid A are known and thought to be TLR 4 agonists including, but not limited to:
OM174 (2-deoxy-6-o-[2-deoxy-2-[(R)-3-dodecanoyloxytetra-decanoylamino]-4-o-phosphono-β-D-glucopyranosyl]-2-[(R)-3-hydroxytetradecanoylamino]-α-D-glucopyranosyldihydrogenphosphate), (WO 95/14026)
OM 294 DP (3S,9R)-3-[(R)-dodecanoyloxytetradecanoylamino]-4-oxo-5-aza-9(R)—[(R)-3-hydroxytetradecanoylamino]decan-1,10-diol,1,10-bis(dihydrogenophosphate) (WO 99/64301 and WO 00/0462)
OM 197 MP-Ac DP (3S-,9R)-3-[(R)-dodecanoyloxytetradecanoylamino]-4-oxo-5-aza-9-[(R)-3-hydroxytetradecanoylamino]decan-1,10-diol,1-dihydrogenophosphate 10-(6-aminohexanoate) (WO 01/46127).

Other suitable TLR-4 ligands, capable of causing a signalling response through TLR-4 (Sabroe et al, JI 2003 p 1630-5) are, for example, lipopolysaccharide from gram-negative bacteria and its derivatives, or fragments thereof, in particular a non-toxic derivative of LPS (such as 3D-MPL). Other suitable TLR agonist are: heat shock protein (HSP) 10, 60, 65, 70, 75 or 90; surfactant Protein A, hyaluronan oligosaccharides, heparan sulphate fragments, fibronectin fragments, fibrinogen peptides and b-defensin-2, muramyl dipeptide (MDP) or F protein of respiratory syncytial virus (RSV). In one embodiment, the TLR agonist is HSP 60, 70 or 90.

TLR Agonists

Rather than a TLR4 agonist, other natural or synthetic agonists of TLR molecules may be used in vaccines or immunogenic composition of the invention. These include, but are not limited to, agonists for TLR2, TLR3, TLR5, TLR6, TLR7, TLR8 and TLR9.

In one embodiment of the present invention, a TLR agonist is used that is capable of causing a signalling response through TLR-1 (Sabroe et al, JI 2003 p 1630-5). Suitably, the TLR agonist capable of causing a signalling response through TLR-1 is selected from: Tri-acylated lipopeptides (LPs); phenol-soluble modulin; *Mycobacterium tuberculosis* LP; S-(2,3-bis(palmitoyloxy)-(2-RS)-propyl)-N-palmitoyl-(R)-Cys-(S)-Ser-(S)-Lys(4)-OH, trihydrochloride (Pam3Cys) LP which mimics the acetylated amino terminus of a bacterial lipoprotein and OspA LP from *Borrelia burgdorferi*.

In a further embodiment, a TLR agonist is used that is capable of causing a signalling response through TLR-2 (Sabroe et al, JI 2003 p 1630-5). Suitably, the TLR agonist capable of causing a signalling response through TLR-2 is one or more of a lipoprotein, a peptidoglycan, a bacterial lipopeptide from *M. tuberculosis, B. burgdorferi, T. pallidum*, peptidoglycans from species including *Staphylococcus aureus*, lipoteichoic acids, mannuronic acids, *Neisseria porins*, bacterial fimbriae, *Yersinia* virulence factors, CMV virions, measles haemagglutinin, and zymosan from yeast.

In a further embodiment, a TLR agonist is used that is capable of causing a signalling response through TLR-3 (Sabroe et al, JI 2003 p 1630-5). Suitably, the TLR agonist capable of causing a signalling response through TLR-3 is double stranded RNA (dsRNA), or polyinosinic-polycytidylic acid (Poly IC), a molecular nucleic acid pattern associated with viral infection.

In an alternative embodiment, a TLR agonist is used that is capable of causing a signalling response through TLR-5 (Sabroe et al, JI 2003 p 1630-5). Suitably, the TLR agonist capable of causing a signalling response through TLR-5 is bacterial flagellin. Said TLR-5 agonist may be flagellin or may be a fragment of flagellin which retains TLR-5 agonist activity. The flagellin can include a polypeptide selected from the group consisting of *H. pylori, S. typhimurium, V. cholera, S. marcesens, S. flexneri, T. pallidum, L. pneumophilia, B. burgdorferei; C. difficile, R. meliloti, A. tumefaciens; R. lupine; B. clarridgeiae, P. mirabilis, B. subtilus, L. moncytogenes, P. aeruginoa* and *E. coli*.

In a particular embodiment, the flagellin is selected from the group consisting of *S. typhimurium* flagellin B (Genbank Accession number AF045151), a fragment of *S. typhimurium* flagellin B, *E. coli* FliC. (Genbank Accession number AB028476); fragment of *E. coli* FliC; *S. typhimurium* flagellin FliC (ATCC14028) and a fragment of *S. typhimurium* flagellin FliC In a further particular embodiment, said TLR-5 agonist is a truncated flagellin, as described in WO 09/156405 i.e. one in which the hypervariable domain has been deleted. In one aspect of this embodiment, said TLR-5 agonist is selected from the group consisting of: $FliC_{A174-400}$; $FliC_{A161-405}$ and $FliC_{A138-405}$.

In a further particular embodiment, said TLR-5 agonist is a flagellin, as described in WO 09/128950.

In a further embodiment, a TLR agonist is used that is capable of causing a signalling response through TLR-6 (Sabroe et al, JI 2003 p 1630-5). Suitably, the TLR agonist capable of causing a signalling response through TLR-6 is mycobacterial lipoprotein, di-acylated LP, and phenol-soluble modulin. Further TLR6 agonists are described in WO 03/043572.

In a further embodiment, a TLR agonist is used that is capable of causing a signalling response through TLR-7 (Sabroe et al, JI 2003 p 1630-5). Suitably, the TLR agonist capable of causing a signalling response through TLR-7 is a single stranded RNA (ssRNA), loxoribine, a guanosine analogue at positions N7 and C8, or an imidazoquinoline compound, or derivative thereof. In a particular embodiment, the TLR agonist is imiquimod. Further TLR7 agonists are described in WO 02/085905.

In a further embodiment, a TLR agonist is used that is capable of causing a signalling response through TLR-8 (Sabroe et al, JI 2003 p 1630-5). Suitably, the TLR agonist capable of causing a signalling response through TLR-8 is a single stranded RNA (ssRNA), an imidazoquinoline molecule with anti-viral activity, for example resiquimod (R848); resiquimod is also capable of recognition by TLR-7. Other TLR-8 agonists which may be used include those described in WO 04/071459.

In a further embodiment, a TLR agonist is used that is capable of causing a signalling response, such as one that comprises a CpG motif. The term "immunostimulatory oligonucleotide" is used herein to mean an oligonucleotide that is capable of activating a component of the immune system. In one embodiment, the immunostimulatory oligonucleotide comprises one or more unmethylated cytosine-guanosine (CpG) motifs. In a further embodiment, the immunostimulatory oligonucleotide comprises one or more unmethylated thymidine-guanosine (TG) motif or may be T-rich. By T-rich, it is meant that the nucleotide composition of the oligonucleotide comprises greater than 50, 60, 70 or 80% thymidine. In one embodiment, the oligonucleotide is not an immunostimulatory oligonucleotide and does not comprise an unmethylated CpG motif. In a further embodiment the immunostimulatory oligonucleotide is not T-rich and/or does not comprise an unmethylated TG motif.

The oligonucleotide may be modified in order to improve in vitro and/or in vivo stability. For example, in one embodiment, the oligonucleotides are modified so as to comprise a phosphorothioate backbone, i.e. internucleotide linkages. Other suitable modifications including diphosphorothioate, phosphoroamidate and methylphosphonate modifications as well as alternative internucleotide linkages to oligonucleotides are well known to those skilled in the art and are encompassed by the invention.

In another embodiment, the vaccines or immunogenic compositions of the invention further comprise an immunostimulant selected from the group consisting of: a TLR-1 agonist, a TLR-2 agonist, TLR-3 agonist, a TLR-4 agonist, a TLR-5 agonist, a TLR-6 agonist, a TLR-7 agonist, a TLR-8 agonist, TLR-9 agonist, or a combination thereof.

Calcium Composites

In some embodiments, the vaccine or immunogenic composition of the invention comprises a calcium fluoride composite, the composite comprising Ca, F, and Z. By "Z" is intended an organic molecule. By "composite" is intended a material that exists as a solid when dry, and that is insoluble, or poorly soluble, in pure water. In some aspects, Z comprises a functional group that forms an anion when ionized. Such functional groups include without limitation one or more functional groups selected from the group consisting of: hydroxyl, hydroxylate, hydroxo, oxo, N-hydroxylate, hydroaxamate, N-oxide, bicarbonate, carbonate, carbon/late, fatty acid, thiolate, organic phosphate, dihydrogenophosphate, monohydrogenophosphate, monoesters of phosphoric acid, diesters of phosphoric acid, esters of phospholipid, phosphorothioate, sulphates, hydrogen sulphates, enolate, ascorbate, phosphoascorbate, phenolate, and imine-olates.

In some aspects, the calcium fluoride composites herein described comprise Z, where Z is an anionic organic molecule possessing an affinity for calcium and forming a water insoluble composite with calcium and fluoride. In further aspects, the calcium fluoride composites herein described comprise Z, where Z may be categorized as comprising a member of a chemical category selected from the group consisting of: hydroxyl, hydroxylates, hydroxo, oxo, N-hydroxylate, hydroaxamate, N-oxide, bicarbonates, carbonates, carboxylates and dicarboxylate, salts of carboxylic-acids, salts of QS21, extract of bark of *Quillaja saponaria*, extract of immunological active saponine, salts of saturated or unsaturated fatty acid, salts of oleic acid, salts of amino-acids, thiolates, thiolactate, salt of thiol-compounds, salts of cysteine, salts of N-acetyl-cysteine, L-2-Oxo-4-thiazolidin-ecarboxylate, phosphates, dihydrogenophosphates, mono-hydrogenophosphate, salts of phosphoric-acids, monoesters of phosphoric acids and their salts, diesters of phosphoric acids and their salts, esters of 3-O-desacyl-4'-monophophoryl lipid A, esters of 3D-MLA, MPL, esters of phospholipids, DOPC, dioleolyphosphatidic derivatives, phosphates from CpG motifs, phosphorothioates from CpG family, sulphates, hydrogen sulphates, salts of sulphuric acids, enolates, ascorbates, phosphoascorbate, phenolate, α-tocopherol, imine-olates, cytosine, methyl-cytosine, uracyl, thymine, barbituric acid, hypoxanthine, inosine, guanine, guanosine, 8-oxo-adenine, xanthine, uric acid, pteroic acid, pteroylglutamic acid, folic acid, riboflavin, and lumiflavin. In further aspects, the calcium fluoride composites herein described comprise Z, where Z is selected from the group consisting of: N-acetyl cysteine; thiolactate; adipate; carbonate; folic acid; glutathione; and uric acid. In some aspects, the calcium fluoride composites herein comprise Z, where Z is selected from the group consisting of: N-acetyl cysteine; adipate; carbonate; and folic acid. In further aspects, the calcium fluoride composites herein comprise Z, where Z is N-acetyl cysteine, and the composite comprises between 51% Ca, 48% F, no more than 1% N-acetyl cysteine (w/w) and 37% Ca, 26% F, and 37% N-acetyl cysteine (w/w). In further aspects, the calcium fluoride composites herein comprise Z, where Z is Z is thiolactate, and the composite comprises between 51% Ca, 48% F, no more than 1% thiolactate (w/w) and 42% Ca, 30% F, 28% thiolactate (w/w). In further aspects, the calcium fluoride composites herein comprise Z, where Z is Z is adipate, and the composite comprises between 51% Ca, 48% F, no more than 1% adipate (w/w) and 38% Ca, 27% F, 35% adipate (w/w). In further aspects, the calcium fluoride composites herein comprise Z, where Z is Z is carbonate, and the composite comprises between 51% Ca, 48% F, no more than 1% carbonate (w/w) and 48% Ca, 34% F, 18% carbonate (w/w). In further aspects, the calcium fluoride composites herein comprise Z, where Z is Z is folic acid, and the composite comprises between 51% Ca, 48% F, no more than 1% folic acid (w/w) and 22% Ca, 16% F, 62% folic acid (w/w). In further aspects, the calcium fluoride composites herein comprise Z, where Z is glutathione, and the composite comprises between 51% Ca, 48% F, no more than 1% glutathione (w/w) and 28% Ca, 20% F, 52% glutathione (w/w). In further aspects, the calcium fluoride composites herein comprise Z, where Z is uric acid, and the composite comprises between 51% Ca, 48% F, and no more than 1% uric acid (w/w) and 36% Ca, 26% F, and 38% uric acid (w/w).

Aluminium Salts

In one embodiment, the vaccine or immunogenic composition of the invention comprises an aluminium salt. Suitable aluminium salt adjuvants are well known to the skilled person and include but are not limited to aluminium phosphate, aluminium hydroxide or a combination thereof. Suitable aluminium salt adjuvants include but are not limited to Rehydragel™ HS, Alhydrogel™ 85, Rehydragel™ PM, Rehydragel™ AB, Rehydragel™ HPA, Rehydragel™ LV, Alhydrogel™ or a combination thereof. In particular, the methods of the invention are used to determine the endotoxin content of Adjuphos, Rehydragel™ HS (3% aluminium hydroxide in water [General Chemical]) or Alhydrogel™ 85 (Brenntag BioSector [Denmark]).

In particular, the aluminium salts may have a protein adsorption capacity of between 2.5 and 3.5, 2.6 and 3.4, 2.7 and 3.3 or 2.9 and 3.2, 2.5 and 3.7, 2.6 and 3.6, 2.7 and 3.5, or 2.8 and 3.4 protein (BSA)/ml aluminium salt. In a particular embodiment of the invention, the aluminium salt has a protein adsorption capacity of between 2.9 and 3.2 mg BSA/mg aluminium salt. Protein adsorption capacity of the aluminium salt can be measured by any means known to the skilled person. The protein adsorption capacity of the aluminium salt may be measured using the method as described in Example 1 of WO 12/136823 (which utilises BSA) or variations thereof.

Aluminium salts described herein (i.e. having the protein adsorption capacity described herein) may have a crystal size of between 2.8 and 5.7 nm as measured by X-ray diffraction, for example 2.9 to 5.6 nm, 2.8 to 3.5 nm, 2.9 to 3.4 nm or 3.4 to 5.6 nm or 3.3 and 5.7 nm as measured by X-ray diffraction. X-ray diffraction is well known to the skilled person. In a particular embodiment of the invention the crystal size is measured using the method described in Example 1 of WO 12/136823 or variations thereof.

Modes of Administration

The pro-resolving mediator may be administered concomitantly, before or after administration of the vaccine or immunogenic composition. Accordingly, the invention provides pro-resolving mediators of the invention for use in the reduction of reactogenicity induced by administration of a vaccine or an immunogenic composition wherein the pre-resolving mediator(s) is (are) administered 5, 10, 20, 30, 45 minutes or more, or 1, 2, 3, 4, 5, 6, 7, 8, 9, or 10 hours or more before administration of the vaccine or immunogenic composition, in particular between 30 minutes and 3 hours, in particular about 1 hour before administration of the vaccine or immunogenic composition.

The invention further provides in some embodiments pro-resolving mediators of the invention for use in the reduction of reactogenicity induced by administration of a vaccine or an immunogenic composition wherein the pre-resolving mediator(s) is (are) administered concomitantly with said vaccine or immunogenic composition. The pro-resolving mediators may be administered at the same time by the same route of administration or by a different route. By "concomitantly", it is meant within up to 5 minutes of administration of the vaccine or immunogenic composition, for example up to 1, 2, 3 or 4 minutes before or after administration of the vaccine or immunogenic composition. In those embodiments where the pro-resolving mediator(s) of the invention is (are) administered concomitantly with the vaccine or immunogenic composition by the same route of administration, said pro-resolving mediator(s) may suitably be formulated with the antigen component and/or the adjuvant component of the vaccine or immunogenic composition. Accordingly, in particular embodiments, the pro-resolving mediator(s) of the invention is (are) formulated with the antigen component of the vaccines or immunogenic compositions of the invention. In further particular embodiments, the pro-resolving mediator(s) of the invention is (are) formulated with the adjuvant component of the vaccines or immunogenic compositions of the invention.

The invention further provides in some embodiments pro-resolving mediators of the invention for use in the reduction of reactogenicity induced by administration of a vaccine or immunogenic composition wherein the pre-resolving mediator(s) is (are) administered 5, 10, 20, 30, 45 minutes or more, or 1, 2, 3, 4, 5, 6, 7, 8, 9, or 10 hours or more after administration of the vaccine or immunogenic composition, in particular between 30 minutes and 3 hours, in particular about 1 hour.

The pro-resolving mediator as described herein may be administered by any route of administration. It may be the same or a different route of administration as the vaccine/immunogenic composition. Accordingly, the invention provides pro-resolving mediators of the invention for use in the reduction of reactogenicity induced by administration of a vaccine or immunogenic composition wherein the pro-resolving mediator is administered by the same route as the vaccine or immunogenic composition.

The invention also provides pro-resolving mediators of the invention for use in the reduction of reactogenicity induced by administration of a vaccine or immunogenic composition wherein the pro-resolving mediator as described herein is administered by a different route as the vaccine or immunogenic composition.

A pro-resolving mediator as described herein may be administered orally, sublingually, intramuscularly, intradermally (e.g. a skin patch with microprojections) or transdermally (e.g. an ointment or cream).

The invention further provides pro-resolving mediators of the invention for use in the reduction of reactogenicity induced by administration of a vaccine or immunogenic composition wherein the pro-resolving mediator as described herein may be administered at the same site on the patient (e.g. upper arm) but by different routes of administration (in particular wherein the vaccine or immunogenic composition is delivered intramuscularly or intradermally and wherein the pro-resolving mediator is delivered transdermally (e.g. an ointment or cream). The cream or ointment comprising the pro-resolving mediator may be administered before, concomitantly, or after the administration of the vaccine/immunogenic composition by intradermal or intramuscular administration.

Pharmaceutically Acceptable Compositions

Pro-resolving mediator(s), vaccine and immunogenic compositions of the invention are pharmaceutically acceptable. They may include components in addition to the pro-resolving mediator(s), antigen(s), and/or adjuvant e.g. they typically include one or more pharmaceutical carrier(s) and/or excipient(s).

The compositions may include preservatives such as thiomersal or 2-phenoxyethanol. In particular embodiments, vaccine or immunogenic compositions of the invention are substantially free from (i.e. less than 5 μg/ml) mercurial material e.g. thiomersal-free. In particular, compositions are free of mercury and any preservative.

Compositions of the invention may be isotonic and thus may comprise a physiological salt, such as a sodium salt. Sodium chloride (NaCl) is preferred, which may be present at between 1 and 20 mg/ml. Other salts that may be present include potassium chloride, potassium dihydrogen phosphate, disodium phosphate dehydrate, magnesium chloride, calcium chloride.

Compositions will generally have an osmolality of between 200 mOsm/kg and 400 mOsm/kg, preferably between 240-360 mOsm/kg, and in particular between 290-310 mOsm/kg.

Compositions of the invention may include one or more buffers. Typical buffers include: a phosphate buffer; a Tris buffer; a borate buffer; a succinate buffer; a histidine buffer; or a citrate buffer. Buffers will typically be included in the 5-20 mM range.

The pH of compositions of the invention may be between 5.0 and 8.1, and more typically between 6.0 and 8.0 e.g. 6.5 and 7.5, or between 7.0 and 7.8.

Kits of the Invention

The pro-resolving mediator(s), antigen(s) and/or adjuvant may be prepared extemporaneously, at the time of delivery. Thus the invention provides kits including the pro-resolving mediator(s), antigen(s) and/or adjuvant ready for mixing. The kits allow the pro-resolving mediator(s), antigen(s) and/or adjuvant to be kept separately until the time of use. This is of particular importance if the pro-resolving mediator is to be administered at a different time or by a different route of administration for example.

Accordingly, the present invention provides kits comprising i) an antigen as described herein; and ii) a pro-resolving mediator as described herein. The present invention also provides kits comprising i) an adjuvant as described herein; and ii) a pro-resolving mediator as described herein. The present invention further provides kits comprising i) an antigen as described herein; (ii) an adjuvant as described herein; and iii) a pro-resolving mediator as described herein.

The components are physically separate from each other within a kit, and this separation can be achieved in various ways. For instance, the two components may be in two separate containers, such as vials. The contents of the two vials can then be mixed e.g. by removing the contents of one vial and adding them to the other vial, or by separately removing the contents of both vials and mixing them in a third container (for example vial).

In a particular embodiment, one of the kit components is in a syringe and the other is in a container, such as a vial. The syringe can be used (e.g. with a needle) to insert its contents into the second container for mixing, and the mixture can then be withdrawn into the syringe. The mixed contents of the syringe can then be administered to a patient, typically through a new sterile needle. Packing one component in a syringe eliminates the need for using a separate syringe for patient administration. In another preferred arrangement, the two kit components are held together but separately in the same syringe e.g. a dual-chamber syringe. When the syringe is actuated (e.g. during administration to a patient) then the contents of the two chambers are mixed. This arrangement avoids the need for a separate mixing step at the time of use.

The kit components may be in aqueous form. In some embodiments, a component such as the antigen(s) or the pro-resolving mediator(s) is in dry form (e.g. in a lyophilised form), with the other component being in aqueous form. The two components can be mixed in order to reactivate the dry component and give an aqueous composition for administration to a patient. A lyophilised component will typically be located within a vial rather than a syringe.

Dried components may include stabilizers such as lactose, sucrose or mannitol, as well as mixtures thereof e.g. lactose/sucrose mixtures, sucrose/mannitol mixtures, etc. One possible arrangement uses an aqueous adjuvant component in a pre-filled syringe and a lyophilised antigen component in a vial.

EXAMPLES

Example 1—Effect of Resolvin E1 (RvE1) on the Local Immune Cells Profile Induced by Adjuvants Injection Mice (n=6/gr) were injected intramuscularly with PBS, AS03 adjuvant (oil-in-water emulsion) or AS01B adjuvant (MPL+QS21 in liposomes). 1 h and 6 h later, synthetic RvE1 (0.2 µg/dose) or PBS was administered also intramuscularly. Muscles were collected at 24 h following adjuvant/PBS administration and local immune cells were extracted. The cells were stained with the following antibodies: Lytic, SiglecF, CD90.2, Ly6G, CD11b, CD11c, HLA DR, CD45 and CD19 and analysed by flow cytometry. The cell recruitment is expressed in number of cells per muscle. The plotted area represents the mean obtained for a specific subpopulation. A 2-way ANOVA was performed to compare the different groups. *: $p<0.05$. The results are shown in FIG. 1. The chemical structure of the synthetic RvE1 used in the present experiment is identical to the chemical structure of RvE1 disclosed in Buckley et al. ("Proresolving Lipid Mediators and Mechanisms in the Resolution of Acute Inflammation", 2014, *Immunity* 40: 315-327).

Results—Conclusions

The injection of each of the adjuvants, AS03 and AS01B, resulted in the recruitment of immune cells to the site of injection, as compared with PBS alone. The injection of RvE1 subsequently to the injection of AS03 adjuvant resulted in a significantly reduced recruitment of all the immune cell types tested. The same conclusion holds true when RvE1 was injected subsequently to the injection of AS01B, indicating that RvE1 used in this experiment was biologically active, as being capable of modulating the pattern of immune cells at the injection site. It is also worth noting that the injection of each adjuvant alone triggered a different pattern of immune cells at the injection site. Also, RvE1 on its own, with PBS alone, did seem to have only a minimal effect on the pattern of immune cells at the injections site, as compared with PBS alone.

Figure 2:
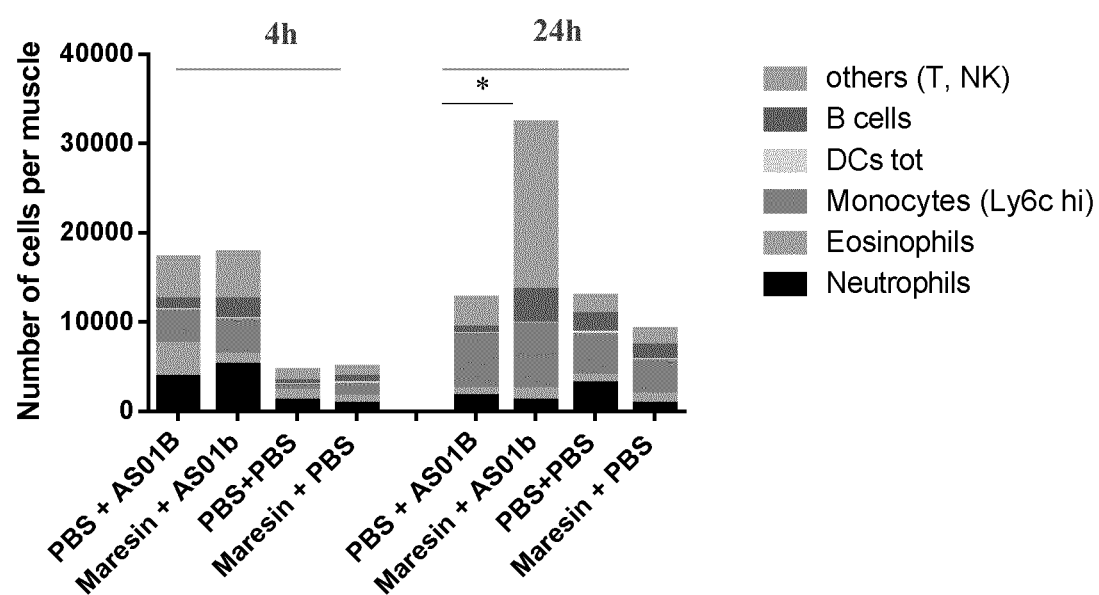
FIG. 2—Effect of 7-Maresin-1 (MaR1) on the local immune cells profile induced by adjuvants injection.

Example 2—Effect of 7-Maresin-1 (MaR1) on the Local Immune Cells Profile Induced by Adjuvants Injection Mice (n=6/gr) were injected intramuscularly with synthetic 7-Maresin-1 (MaR1) (5 ng/dose) or PBS as a control. 1 h later, mice received intramuscularly adjuvant AS01B or PBS. Muscles were collected at 4 h and 24 h following 7-Maresin-1/PBS administration and local immune cells were extracted. The cells were stained with the following antibodies: Lytic, SiglecF, CD90.2, Ly6G, CD11b, CD11c, HLA DR, CD45 and CD19 and analysed by flow cytometry. The cell recruitment is expressed in number of cells per muscle. The plotted area represents the mean obtained for a specific subpopulation. A 2-way ANOVA was performed to compare the different groups. *: $p<0.05$. The results are shown in FIG. 2. The chemical structure of the synthetic MaR1 used in the present experiment is identical to the chemical structure of MaR1 disclosed in Buckley et al. ("Proresolving Lipid Mediators and Mechanisms in the Resolution of Acute Inflammation", 2014, *Immunity* 40: 315-327).

Results—Conclusions

When injecting MaR1 prior to injecting the adjuvant AS01B, the most significant modulating effect observed on the pattern of immune cells at the injection site was achieved at 24 h post-injection, confirming that in this experiment MaR1 was biologically active. The major changes observed were an increase of B cells and T cells recruitment on site, which is a feature of late resolution phase. This suggests that the observation of a modulating effect of MaR1 may be dependent on the time post-injection, and that 4 h post-injection may be too early to detect an effect.

Figure 3:
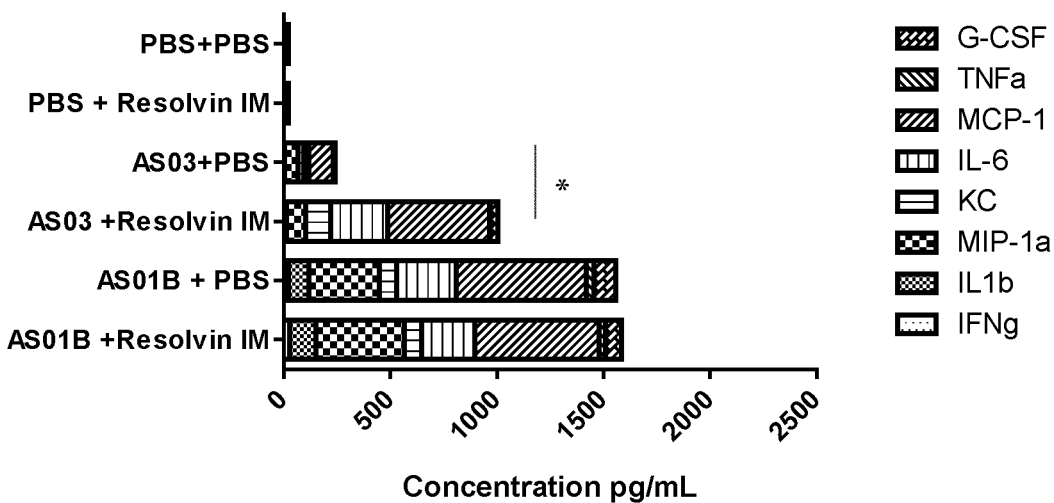
FIG. 3—Effect of Resolvin E1 (RvE1) on the local cytokine profile induced by adjuvants injection.
Figure 3:
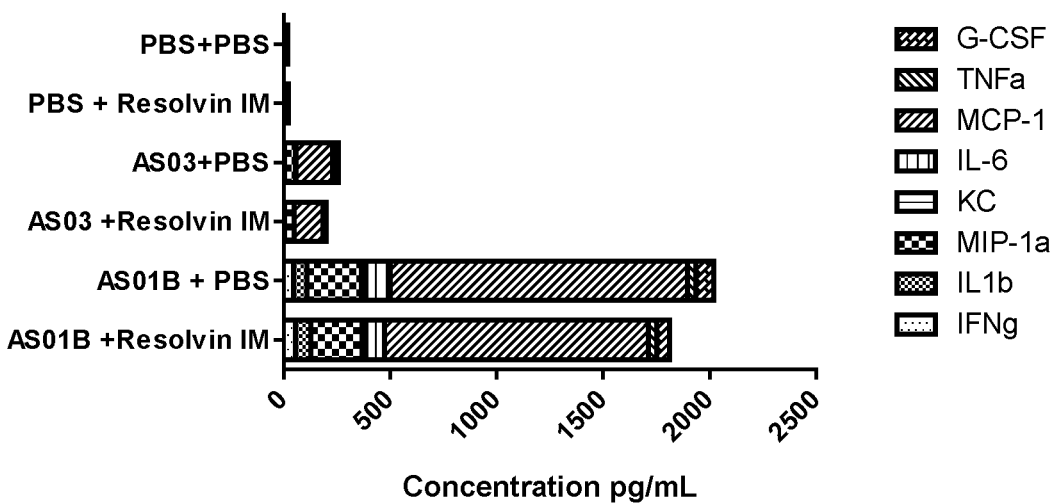

Example 3—Effect of Resolvin E1 (RvE1) on the Local Cytokine Profile Induced by Adjuvants Injection Mice (n=6/gr) were injected intramuscularly with PBS, adjuvant AS03 or adjuvant AS01B. 1 h and 6 h later, the same synthetic RvE1 as the one used in Example 1 (0.2 µg/dose), or PBS was administered also intramuscularly. Muscles were collected at 4 h (A) and 24 h (B) following adjuvant or PBS administration and frozen at −70° C. Muscles were thawed and homogenized and cytokines (TNFα, IL-6, IL1b and IFNγ) and chemokine (G-CSF, MCP-1, KC and MIP-1a) levels in the cleared homogenates were measured by CBA (Becton Dickinson). The cytokine/chemokine concentrations are expressed in pg/mL. The plotted area represents the mean obtained for a specific cytokine/chemokine. A 2-way ANOVA was performed to compare the different groups. *: $p<0.05$ (See FIG. 3).

Results—Conclusions

The injection of each of the adjuvants, AS03 and AS01B, resulted in an increase of the cytokines/chemokines concentration at the injection site, as compared with PBS alone, to different extent. With regard to the adjuvant AS01B, no significant modulating effect was observed when injecting RvE1 subsequently to the adjuvant injection at the two time points tested, that is 4 h and 24 h post-injection of the adjuvant (see panel A and panel B, respectively, of FIG. 3). With regard to the adjuvant AS03, a significant modulating effect was observed when injecting RvE1 subsequently to the adjuvant injection at 4 h post-injection of the adjuvant, while no significant effect was observed at 24 h post-injection of the adjuvant. These results indicate that the RvE1 used in this experiment was biologically active, as being capable of modulating the cytokines/chemokines concentration at the injection site. Said results also suggest that the ability of RvE1 to modulate the local cytokines/chemokines profile may differ depending on the type of adjuvant which is injected and/or that the modulating effect may be observed at different time points post-injection of the adjuvant.

Example 4—Effect of 7-Maresin-1 (MaR1) on the Local Cytokine Profile Induced by Adjuvants Injection Mice (n=6/gr) were injected intramuscularly with the same synthetic MaR1 as the one used in Example 2 (5 ng/dose), or PBS as a control. 1 h later, mice received intramuscularly adjuvant AS01B or PBS. Muscles were collected at 4 h and 24 h following MaR1/PBS administration and frozen at −70° C. Muscles were thawed and homogenized and cytokines (TNFα, IL-6, IL1b and INFγ) and chemokine (G-CSF, MCP-1, KC and MIP-1a) levels in the cleared homogenates were measured by CBA (Becton Dickinson). The cytokine/chemokine concentrations are expressed in pg/mL. The plotted area represents the mean obtained for a specific cytokine/chemokine. A 2-way ANOVA was performed to compare the different groups. *: $p<0.05$ (See FIG. 4).

Results—Conclusions

The injection of each of the adjuvant AS01B resulted in an increase of the cytokines/chemokines concentration at the injection site, as compared with PBS alone. A significant transient modulating effect was observed when injecting MaR1 prior to the adjuvant injection at 4 h post-injection of the MaR1. These results indicate that the MaR1 used in this experiment was biologically active, as being capable of modulating the local cytokines/chemokines profile at the injection site.

Example 5—No Effect of 7-Maresin-1 (MaR1) on Specific T Cell Responses Induced by Vaccines Injection Mice (n=30/gr) were injected intramuscularly with the same synthetic MaR1 as the one used in Example 2 (5 ng/dose) or PBS as a control. 1 h later, mice were vaccinated with OVA (Ovalbumin) and HBS (Hepatitis B Surface) antigens re-suspended in adjuvant AS01B or in PBS. This vaccination scheme was repeated 15 days later. Spleens were removed 7 days after the second immunization, and immune cells were extracted and stimulated overnight with OVA (A) or HBS (B) peptides. After surface staining with anti-CD4 and anti-CD8 antibodies, cells were labeled intra-cellularly with anti-IL-2, anti-IFN-γ and anti-TNF-α and analyzed by flow cytometry. Results are expressed as percentages of CD4+ or CD8+ T cells expressing at least 2 cytokines among the ones tested. Each point represents an individual value, the bar represents the mean+/−SD (see FIG. 5).

Results—Conclusions

The injection of both OVA and HBS antigens in combination with the adjuvant AS01B induced a significant CD4+ T cell response, as well as a significant CD8+ T cell response, as compared with the injection antigens alone. When injecting MaR1 prior to injecting the antigens in combination with the adjuvant AS01B, neither the CD4+ T cell response, nor the CD8+ T cell response was observed to be statistically inferior to the responses induced by the antigens and the adjuvant alone (see both Panels A and B of FIG. 5). These results indicate that MaR1 injection did not negatively impact the T cell immune response induced by injection of an adjuvanted vaccine.

Example 6—No Effect of 7-Maresin-1 (MaR1) on Specific Antibody Responses Induced by Vaccine Injection Mice (n=30/gr) were injected intramuscularly with the same synthetic MaR1 as the one used in Example 2 (5 ng/dose), or PBS as a control. 1 h later, mice were vaccinated with OVA and HBS antigens re-suspended in adjuvant AS01B or in PBS. This vaccination scheme was repeated 15 days later. Sera were taken 7 days after the second immunization. Anti-OVA (A) or anti-HBs (B) antibodies were detected by ELISA. Antibody titers are expressed in ng/mL. Each point represents an individual value; the bar represents the mean+/−SD. (See FIG. 6).

Results—Conclusions

The injection of both OVA and HBS antigens in combination with the adjuvant AS01B induced a significant anti-OVA antibody response (see Panel A of FIG. 6) and a significant anti-HBS antibody response (see Panel B of FIG.

6), as compared with the injection antigens alone. When injecting MaR1 prior to injecting the antigens in combination with the adjuvant AS01B, neither the anti-OVA antibody response (see Panel A of FIG. 6), nor the anti-HBS antibody response were observed to be statistically inferior to the responses induced by the antigens and the adjuvant alone. These results indicate that MaR1 injection did not negatively impact the antibody immune response induced by injection of an adjuvanted vaccine.

GENERAL CONCLUSIONS

Intramuscular administration of small concentration of pro-resolution mediators, such as RvE1 and MaR1, can modulate the immune cell recruitment profile as well as the local cytokine profile (FIGS. 1, 2, 3 and 4)

The timing of administration and the nature of the pro-resolution mediator administered may modulate differently the local inflammatory profile induced by adjuvants (FIGS. 1, 2, 3 and 4).

Figure 4:
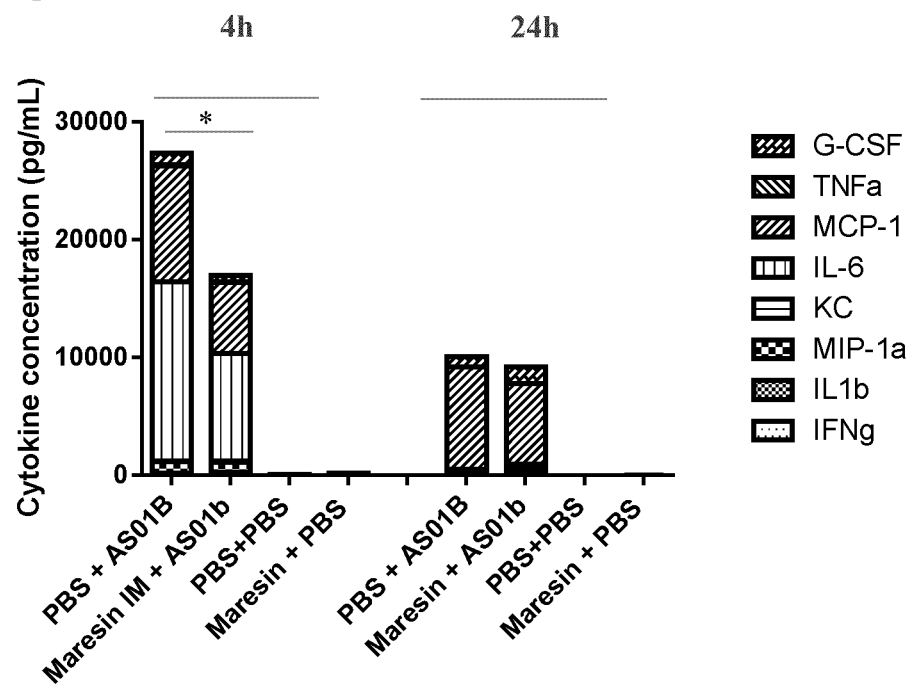
FIG. 4—Effect of 7-Maresin-1 (MaR1) on the local cytokine profile induced by adjuvants injection.

The main local cytokines modulated by the administration of pro-resolution mediators are IL-6 and MCP-1 (FIG. 3A, FIG. 4).

The main local immune cells modulated by the administration of pro-resolution mediators are lymphoid cells and monocytes (FIGS. 1 and 2).

Pro-resolution mediators can modulate the local inflammatory profile induced by two different adjuvants (AS01B and AS03), which modulation, and the extent of which, may differ depending on the adjuvant, and on whether considering the local immune cell recruitment profile or the local cytokine profile.

Figure 5:
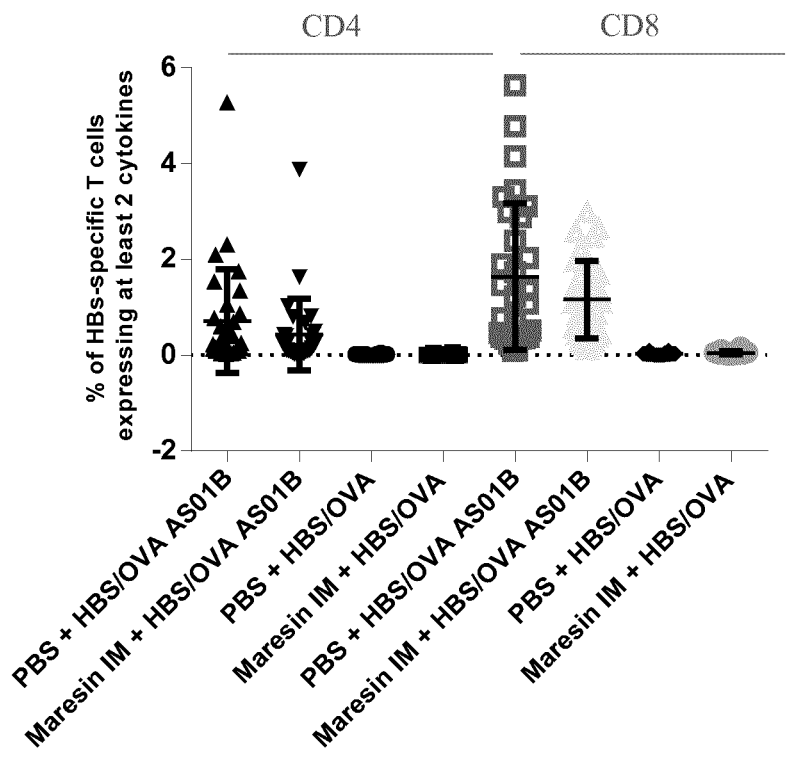
FIG. 5—No Effect of 7-Maresin-1 (MaR1) on specific T cell responses induced by vaccines injection.
Figure 5:
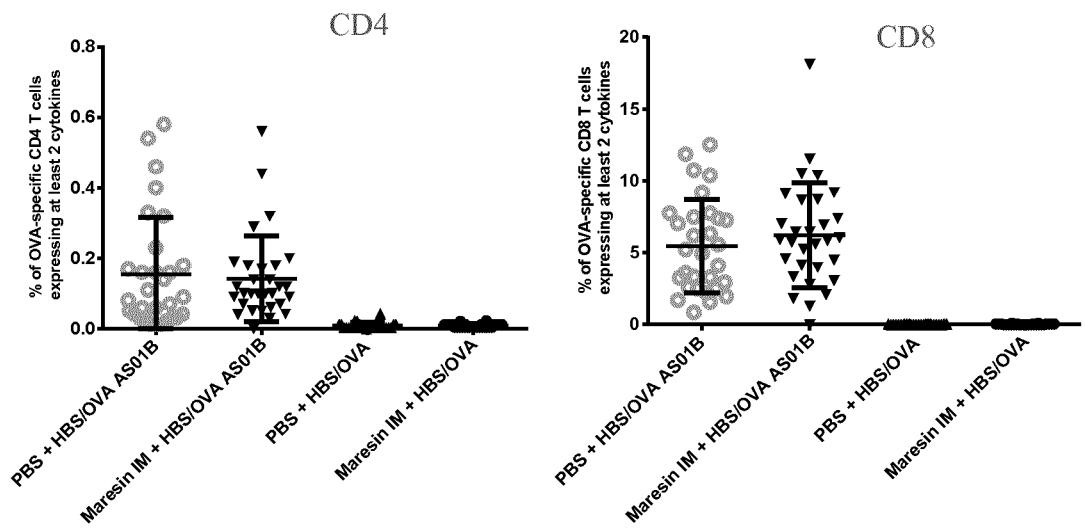
Figure 6:
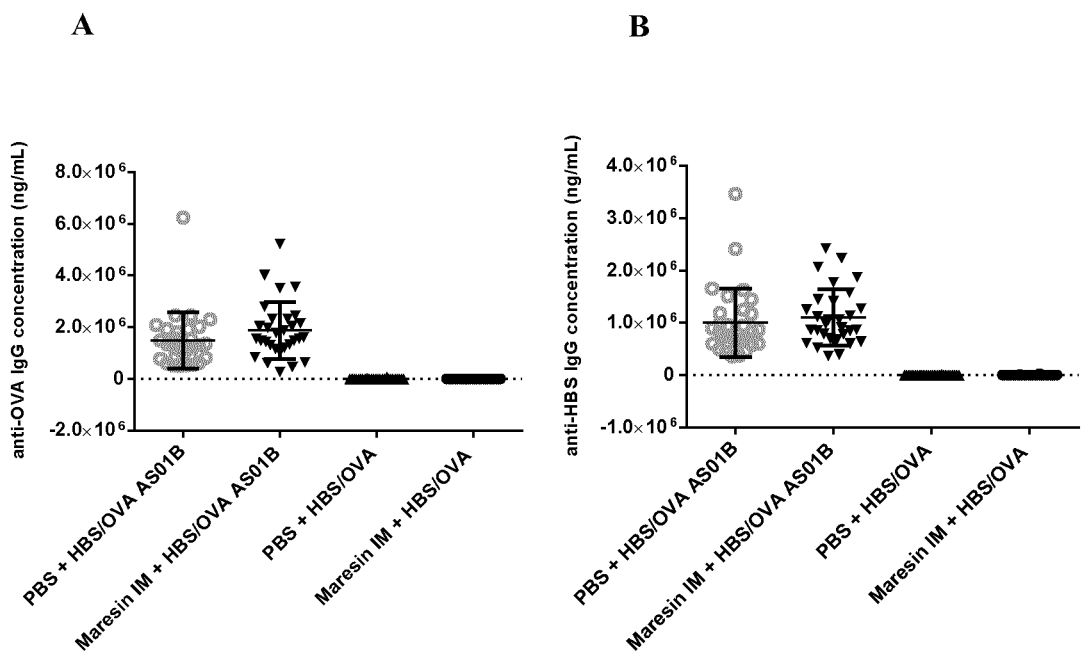
FIG. 6—No effect of 7-Maresin-1 (MaR1) on specific antibody responses induced by vaccine injection.

The local administration of pro-resolution mediators has no impact on vaccine specific T cell and antibody responses (FIGS. 5 and 6).

The invention claimed is:

1. A method of reducing reactogenicity induced by administration of a vaccine or immunogenic composition comprising at least one antigen, said method comprising:
    administering a pro-resolving mediator, which is separate from said vaccine or immunogenic composition, wherein said pro-resolving mediator is administered before, concurrently with, or after the administration of a vaccine or immunogenic composition comprising an antigen and an adjuvant selected from the group consisting of an oil-in-water emulsion, liposomes, a saponin, a TLR4 (toll-like receptor 4) agonist and ISCOMS (immune stimulating complexes), or any combination of two or more thereof,
    wherein the pro-resolving mediator is selected from the group consisting of: a resolvin (E-series or D-series), a maresin, a lipoxin, and a protectin, or any combination of two or more thereof, and
    wherein the pro-resolving mediator promotes resolution of the inflammatory response, thereby reducing reactogenicity.

2. The method of claim 1, wherein the pro-resolving mediator is selected from the group consisting of: Resolvin E1, Resolvin E2, Resolvin E3, Resolvin D1, Resolvin D2, Resolvin D3, Resolvin D4, 7-Maresin-1, protectin D1/neuroprotectin D1, 17-hydroxydocosahexaenoic acid, lipoxin $A_4$ or any combination of two or more thereof.

3. The method of claim 1, wherein the pro-resolving mediator is administered 5, 10, 20, 30, 45 minutes or more, or 1, 2, 3, 4, 5, 6, 7, 8, 9, or 10 hours or more before administration of the vaccine or immunogenic composition.

4. The method of claim 1, wherein the pro-resolving mediator is administered 5, 10, 20, 30, 45 minutes or more, or 1, 2, 3, 4, 5, 6, 7, 8, 9, or 10 hours or more after administration of the vaccine or immunogenic composition.

5. The method of claim 1, wherein the pro-resolving mediator is administered by the same route as the vaccine or immunogenic composition.

6. The method of claim 1, wherein the pro-resolving mediator is administered by a different route as the vaccine or immunogenic composition.

7. The method of claim 1, wherein the pro-resolving mediator is administered orally, sublingually, intramuscularly, intradermally or transdermally.

8. The method of claim 6, wherein the pro-resolving mediator is administered at the same site as the vaccine or immunogenic composition.

9. The method of claim 8, wherein the vaccine or immunogenic composition is delivered intramuscularly or intradermally, and wherein the pro-resolving mediator is delivered transdermally.

10. The method of claim 1, wherein the adjuvant is a saponin and/or a TLR4 (toll-like receptor 4) agonist.

11. The method of claim 1, wherein the antigen is selected from the group consisting of: a whole-organism, a polypeptide, a polysaccharide, a peptide, a nucleic acid and a protein-polysaccharide conjugate, or any combination of two or more thereof.

12. The method of claim 1, wherein said adjuvant is an oil-in-water emulsion.

13. The method of claim 10, wherein the saponin is obtained from a Quil A fraction.

14. The method of claim 1, wherein the adjuvant is QS21.

15. The method of claim 10, wherein the TLR4 agonist is a detoxified lipopolysaccharide.

16. The method of claim 15, wherein the detoxified-lipopolysaccharide is 3D-MPL.

17. The method of claim 10, wherein the saponin and/or TLR4 agonist is in a liposomal formulation.

18. The method of claim 10, wherein the saponin is QS21.

19. The method of claim 10, wherein the pro-resolving mediator is administered before the administration of the vaccine or immunogenic composition.

20. The method of claim 10, wherein the pro-resolving mediator is administered concurrently with the administration of the vaccine or immunogenic composition.

21. The method of claim 10, wherein the pro-resolving mediator is administered after the administration of the vaccine or immunogenic composition.

* * * * *